United States Patent
Zheng et al.

(10) Patent No.: US 11,704,796 B2
(45) Date of Patent: Jul. 18, 2023

(54) ESTIMATING BONE MINERAL DENSITY FROM PLAIN RADIOGRAPH BY ASSESSING BONE TEXTURE WITH DEEP LEARNING

(71) Applicant: Ping An Technology (Shenzhen) Co., Ltd., Shenzhen (CN)

(72) Inventors: Kang Zheng, Bethesda, MD (US); Yirui Wang, Bethesda, MD (US); Shun Miao, Bethesda, MD (US); Changfu Kuo, Taiwan (CN); Chen-I Hsieh, Taiwan (CN)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 291 days.

(21) Appl. No.: 17/142,187

(22) Filed: Jan. 5, 2021

(65) Prior Publication Data

US 2021/0212647 A1 Jul. 15, 2021

Related U.S. Application Data

(60) Provisional application No. 62/988,713, filed on Mar. 12, 2020, provisional application No. 62/988,628, (Continued)

(51) Int. Cl.
*G06T 7/00* (2017.01)
*G06T 7/73* (2017.01)
(Continued)

(52) U.S. Cl.
CPC ............ *G06T 7/0012* (2013.01); *A61B 6/469* (2013.01); *A61B 6/505* (2013.01); *A61B 6/5217* (2013.01);
(Continued)

(58) Field of Classification Search
CPC ....... A61B 6/505; A61B 6/469; A61B 6/5217; G06T 7/11; G06T 7/73; G06T 7/0012;
(Continued)

(56) References Cited

U.S. PATENT DOCUMENTS 5,342,366 A * 8/1994 Whiteside .............. A61B 90/06
606/86 R
9,237,949 B2 * 1/2016 Podolsky ............. A61B 17/164
(Continued)

OTHER PUBLICATIONS

Pickhardt PJ, Pooler BD, Lauder T, del Rio AM, Bruce RJ, Binkley N. Opportunistic screening for osteoporosis using abdominal computed tomography scans obtained for other indications. Ann Intern Med. Apr. 16, 2013;158(8):588-95. doi: 10.7326/0003-4819-158-8-201304160-00003. PMID: 23588747; PMCID: PMC3736840.*

*Primary Examiner* — Shefali D Goradia
(74) *Attorney, Agent, or Firm* — Anova Law Group, PLLC

(57) ABSTRACT

The present disclosure provides a computer-implemented method, a device, and a computer program product for radiographic bone mineral density (BMD) estimation. The method includes receiving a plain radiograph, detecting landmarks for a bone structure included in the plain radiograph, extracting an ROI from the plain radiograph based on the detected landmarks, estimating the BMD for the ROI extracted from the plain radiograph by using a deep neural network.

18 Claims, 15 Drawing Sheets

Related U.S. Application Data filed on Mar. 12, 2020, provisional application No. 62/958,965, filed on Jan. 9, 2020.

(51) Int. Cl.

| | |
|---|---|
| *G06N 3/08* | (2023.01) |
| *A61B 6/00* | (2006.01) |
| *G06T 7/11* | (2017.01) |
| *G06N 3/04* | (2023.01) |
| *G16H 30/40* | (2018.01) |
| *G16H 50/30* | (2018.01) |
| *G06F 18/213* | (2023.01) |
| *G06V 10/764* | (2022.01) |
| *G06V 10/82* | (2022.01) |
| *G06V 10/44* | (2022.01) |

(52) U.S. Cl.
CPC ............ *G06F 18/213* (2023.01); *G06N 3/04* (2013.01); *G06N 3/08* (2013.01); *G06T 7/11* (2017.01); *G06T 7/73* (2017.01); *G06V 10/44* (2022.01); *G06V 10/764* (2022.01); *G06V 10/82* (2022.01); *G16H 30/40* (2018.01); *G16H 50/30* (2018.01); *G06T 2207/10116* (2013.01); *G06T 2207/20072* (2013.01); *G06T 2207/20081* (2013.01); *G06T 2207/20084* (2013.01); *G06T 2207/30012* (2013.01); *G06T 2207/30052* (2013.01); *G06T 2207/30168* (2013.01); *G06V 2201/033* (2022.01)

(58) Field of Classification Search
CPC . G06T 2207/20084; G06T 2207/30012; G06T 2207/30052; G06T 2207/30168; G06T 2207/10116; G06T 2207/20072; G06T 2207/20081; G16H 50/30; G16H 30/40; G06V 10/426; G06V 2201/033; G06K 9/6232; G06N 3/04; G06N 3/08
See application file for complete search history.

(56) References Cited

U.S. PATENT DOCUMENTS

| | | | | |
|---|---|---|---|---|
| 10,588,589 | B2* | 3/2020 | Bregman-Amitai | G16H 50/30 |
| 2004/0242987 | A1* | 12/2004 | Liew | A61B 6/482 |
| | | | | 600/407 |
| 2016/0113612 | A1* | 4/2016 | Sedlmair | G16H 50/30 |
| | | | | 600/408 |

* cited by examiner

ESTIMATING BONE MINERAL DENSITY FROM PLAIN RADIOGRAPH BY ASSESSING BONE TEXTURE WITH DEEP LEARNING

CROSS-REFERENCE TO RELATED APPLICATIONS

This application claims the priority of U.S. Provisional Patent Application No. 62/958,965, filed on Jan. 9, 2020, No. 62/988,628, filed on Mar. 12, 2020, and No. 62/988,713, filed on Mar. 12, 2020, the entire content of all of which are incorporated herein by reference.

THE FIELD OF THE DISCLOSURE

The present disclosure generally relates to the field of image processing and, more particularly, relates to methods, devices, and computer program products for estimating bone mineral density from plain radiographs by assessing bone texture through deep learning.

BACKGROUND

Osteoporosis is a common bone disease that affects over 200 million people worldwide. The main consequence of osteoporosis is fragility fractures, which cause significant morbidity, mortality, and public health expenditures, particularly for women older than 55 years and men older than 65 years. According to the Global Burden of Disease Study 2010, global deaths and associated health burden attributable to osteoporosis almost doubled between 1990 and 2010. Despite the availability of accurate fracture risk assessments and therapeutic options to prevent fractures, osteoporosis is still underdiagnosed and undertreated. Dual-energy X-ray absorptiometry (DXA) is the current modality of choice for low bone mineral density (BMD) screening, and is used to estimate the ten-year osteoporotic fracture risk provided by the fracture risk assessment tool. However, many people with low BMD are asymptomatic, and thus hardly have an opportunity to be screened for bone density by DXA.

In this context, a technique to screen for osteoporosis using plain radiographs may be desirable, since a plain radiograph has greater availability and broader indications, and more importantly, it can be performed much more frequently than DXA. Therefore, plain radiograph screening may provide additional opportunities to identify individuals with osteoporosis risk. The clinical value of this "opportunistic" prediction approach seems apparent since it offers low cost and improves the chance of identifying at-risk patients.

Plain radiography is a relatively cheap imaging technology that provides excellent spatial resolution, enabling high-fidelity visualization of the fine bone texture crucial to bone strength and bone health. More importantly, the bone texture may be directly correlated with the BMD. To date, several different methods for deciphering bone microarchitecture using plain radiographs have occurred. However, most of these approaches use rule-based methods. For example, the H index and fractal analysis are rule-based methods for describing radiographic bone texture and distinguishing patients with osteoporotic fractures from control groups. Semiquantitative visual assessment of osteoporosis based on trabeculation shown in plain radiographs can only provide a rough estimate of osteoporosis. Further, assessing BMD from a plain radiograph is difficult even for experienced physicians, and the qualitative nature of visual assessment is inadequately accurate to support clinical decisions regarding patient management.

Therefore, there is a need for approaches to estimating BMD using plain radiographs, to enable opportunistic osteoporosis screening.

BRIEF SUMMARY OF THE DISCLOSURE

According to one aspect of the present disclosure, a computer-implemented method for radiographic BMD estimation is provided. The method includes receiving a plain radiograph, detecting landmarks for a bone structure included in the plain radiograph, extracting an ROI from the plain radiograph based on the detected landmarks, and estimating the BMD for the ROI extracted from the plain radiograph by using a deep neural network.

According to another aspect of the present disclosure, a device for image landmark detection is provided. The device includes a processor and a non-transitory memory communicatively coupled to the processor. The memory contains computer programs that, when executed by the processor, cause the processor to implement operations that include receiving a plain radiograph, detecting landmarks for a bone structure included in the plain radiograph, extracting an ROI from the plain radiograph based on the detected landmarks, and estimating the BMD for the ROI extracted from the plain radiograph by using a deep neural network.

According to yet another aspect of the present disclosure, a computer program product for image landmark detection is provided. The computer program product includes a non-transitory computer-readable storage medium and program instructions stored therein, where the program instructions are configured to be executable by a computer to cause the computer to perform operations that include receiving a plain radiograph, detecting landmarks for a bone structure included in the plain radiograph, extracting an ROI from the plain radiograph based on the detected landmarks, and estimating the BMD for the ROI extracted from the plain radiograph by using a deep neural network.

Other embodiments of one or more of these aspects and other aspects include corresponding apparatus, and computer programs, configured to perform the various actions and/or store various data described in association with these aspects. Numerous additional features may be included in these and various other embodiments, as discussed throughout this disclosure It should be understood that the language used in the present disclosure has been principally selected for readability and instructional purposes, and not to limit the scope of the subject matter disclosed herein.

BRIEF DESCRIPTION OF THE DRAWINGS

The accompanying drawings, which are incorporated in and constitute a part of the specification, illustrate various embodiments of the present disclosure and, together with the description, serve to explain the principles of the present disclosure.

DETAILED DESCRIPTION

The figures and the following description relate to some embodiments by way of illustration only. It should be noted that from the following discussion, alternative embodiments of the structures and methods disclosed herein will be readily recognized as viable alternatives that may be employed without departing from the spirits and principles of the present disclosure.

Devices and methods consistent with the present disclosure are directed to a texture-based deep learning model for effective estimation of BMD from a plain radiograph. According to some embodiments of the present disclosure, the plain radiograph may be first subject to a landmark detection model developed to formulate the anatomical landmarks of certain bone structures (e.g., pelvis or spines) as a graph and robustly and accurately detect anatomical landmarks to locate the bone structures (e.g., hips). A region of interest may be automatically extracted based on the detected anatomical landmarks. The extracted ROI is further augmented, and then input into a BMD estimation model, to estimate the BMD for the extracted ROI.

The disclosed methods and devices have great clinical diagnosis advantages. Osteoporosis is under-detected due to the under-application (or limited availability) of DXA in asymptomatic patients with osteoporosis; therefore, a tool designed to detect osteoporosis from plain radiographs (may be also referred to as "plain films") could improve the chance of at-risk patients being screened and referred for definitive therapy. In areas with limited DXA availability, because the availability of plain films is much larger than the availability of DXA, the disclosed methods and devices can serve as the primary tool for identifying patients at risk of osteoporosis.

Exemplary embodiments are now described with reference to the accompanying drawings. In the figures, the left-most digit(s) of a reference number identifies the figure in which the reference number first appears. Wherever convenient, the same reference numbers are used throughout the drawings to refer to the same or like parts.

Figure 1:
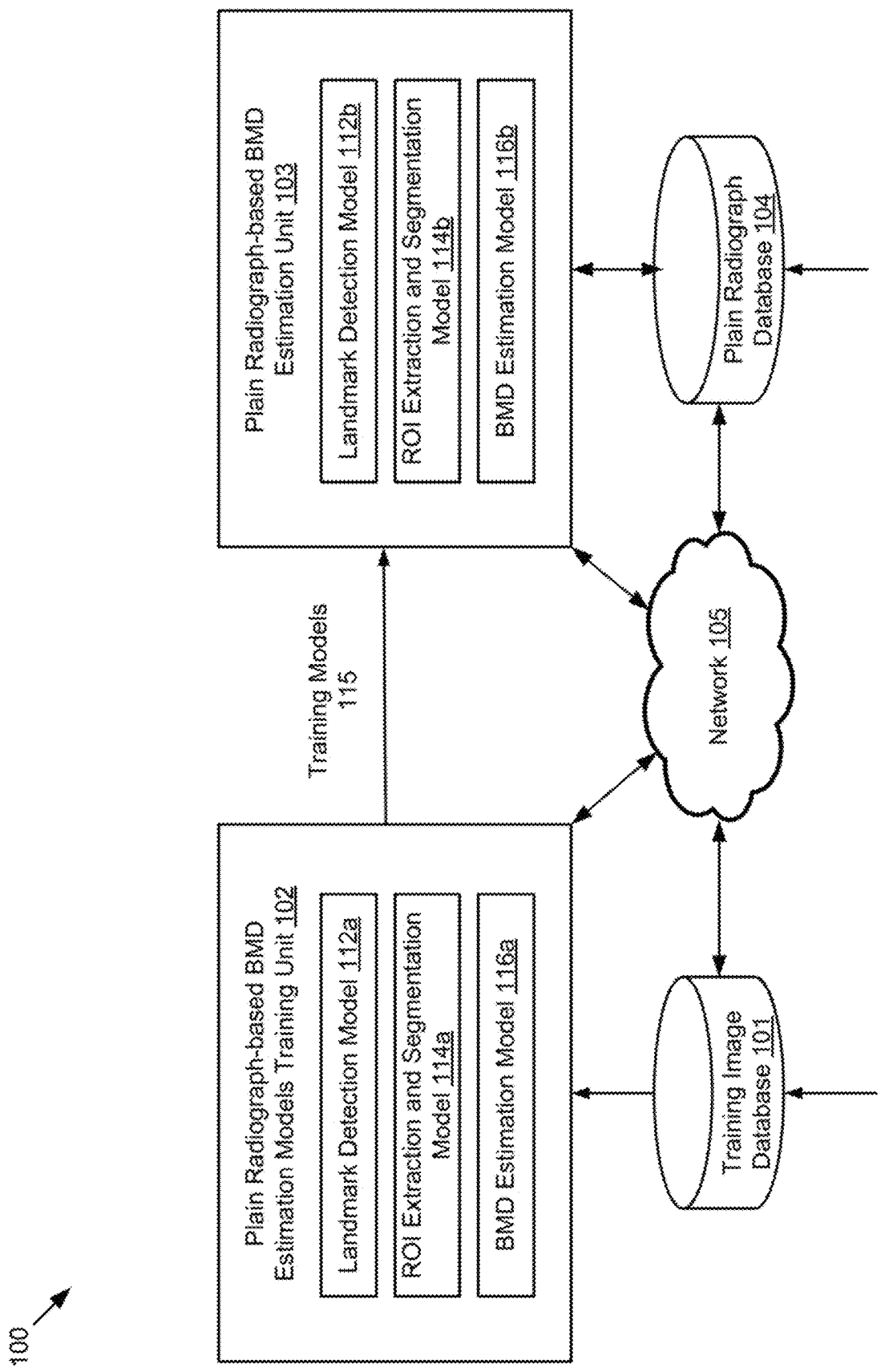
FIG. 1 illustrates an exemplary plain radiograph-based BMD estimation system, according to some embodiments of the present disclosure.

FIG. 1 illustrates an exemplary plain radiograph-based BMD estimation system 100, according to some embodiments of the present disclosure. Plain radiograph-based BMD estimation system 100 may include a training image database 101, a plain radiograph-based BMD estimation model training unit 102, a plain radiograph-based BMD estimation unit 103, a plain radiograph database 104, and a network 105. The plain radiograph-based BMD estimation model training unit 102 may further include a pre-trained landmark detection model 112a, an ROI extraction and segmentation model 114a, and a BMD estimation model 116a, while the plain radiograph-based BMD estimation unit 103 may further include a trained landmark detection model 112b, an ROI extraction and segmentation model 114b, and a BMD estimation model 116b (models 112b, 114b, and 116b together may be referred to as "plain radiograph-based BMD estimation model").

In some embodiments, plain radiograph-based BMD estimation system 100 may include more or fewer of the components illustrated in FIG. 1. For example, when models used for plain radiograph-based BMD estimation are pre-trained and provided, plain radiograph-based BMD estimation system 100 may only contain plain radiograph-based BMD estimation unit 103, plain radiograph database 104, and, optionally, network 105.

In some embodiments, the various components of the plain radiograph-based BMD estimation system 100 may be located remotely from each other and be connected through network 105. For example, landmark detection model 112b, ROI extraction and segmentation model 114b, BMD estimation model 116b applied for plain radiograph-based BMD estimation may be located remotely from each other and/or be connected through network 105. Similarly, pre-trained landmark detection model 112a, ROI extraction and segmentation model 114a, and BMD estimation model 116a may be located remotely from each other and/or connected through network 105. In some alternative embodiments, certain components of the plain radiograph-based BMD estimation system 100 may be located on a same site or inside one device. For example, training image database 101 may be located on-site with the plain radiograph-based BMD estimation model training unit 102, or be part of the plain radiograph-based BMD estimation model training unit 102. As another example, plain radiograph-based BMD estimation model training unit 102 and plain radiograph-based BMD estimation unit 103 may be inside a same computer or image processing device.

As shown in FIG. 1, plain radiograph-based BMD estimation model training unit 102 may communicate with training image database 101 to receive one or more training images or image datasets. The training images or image datasets stored in training image database 101 may be obtained from different sources and may contain a medical image (such as X-ray images, CT images, other radiographs and non-radiograph images) and/or non-medical images (such as facial images). In some embodiments, the training images may be pre-treated, curated, or resized. In some embodiments, the training images may be further labelled or annotated. Depending on the purposes, different training images may be labelled or annotated differently. For instance, some training images may be labeled or annotated for training landmark detection model 112a, some training images may be labeled or annotated for training ROI extraction and segmentation model 114a, and some training images may be labeled or annotated for training BMD estimation model 116a.

Plain radiograph-based BMD estimation model training unit 102 may train each of the landmark detection model 112a, ROI extraction and segmentation model 114a, and BMD estimation model 116a individually or as a single model. To train the models 112a, 114a, and 116a individually, each of the models 112a, 114a, and 116a may be pre-trained separately by plain radiograph-based BMD estimation model training unit 102. Accordingly, in some embodiments, there may be one or more plain radiograph-based BMD estimation model training units 102, each being responsible for training one or more of the models 112a, 114a, and 116a. To train the models 112a, 114a, ad 116a as a single model, the three models 112a, 114a, and 116a may be properly configured for data transmission among the models 112a, 114a, and 116a, which are then trained as a single model by inputting the training data to the model 112a. When the three models 112a, 114a, and 116a are trained as a single model, one or more of the models 112a, 114a, or 116a may be already pre-trained before being trained as a single model. Alternatively, one or more of the models 112a, 114a, or 116a are not pre-trained before being trained as a single model. In some embodiments, if more than one plain radiograph-based BMD estimation model training unit 102 is used for training, these plain radiograph-based BMD estimation model training units 102 may be located within a same or different computing device located at a same or different location.

As previously discussed, each of the landmark detection model 112a, ROI extraction and segmentation model 114a, and BMD estimation model 116a may be trained with corresponding training data or datasets that may be labeled, marked, curated, and/or annotated differently for each model. These training data or datasets may be respectively fed into each model for training the corresponding model. The training process for each model may end upon at least one of the following conditions is satisfied: (1) training time exceeds a predetermined time length; (2) number of iterations exceed a predetermined iteration threshold; (3) a calculated loss function (e.g., a cross-entropy loss function) is smaller than a predetermined loss threshold. If the loss function is used, different models may each have a corresponding loss function developed for the corresponding model.

In some embodiments, after each landmark detection model 112a, ROI extraction and segmentation model 114a, and BMD estimation model 116a is trained, the trained landmark detection model 112b, ROI extraction and segmentation model 114b, and BMD estimation model 116b may be deployed into the plain radiograph-based BMD estimation unit 103 for actual plain radiograph-based BMD estimation.

In some embodiments, to allow the trained landmark detection model 112b, ROI extraction and segmentation model 114b, and BMD estimation model 116b to work properly in plain radiograph-based BMD estimation, the trained models 112b, 114b, and 116b may be configured right after being deployed into the plain radiograph-based BMD estimation unit 103. For instance, the trained landmark detection model 112b may be configured to receive an original plain radiograph (e.g., an anterior-posterior pelvis plain film) as an input image, formulate the anatomical landmarks of the bone structures in the radiograph as a graph, and robustly and accurately detect the anatomical landmarks to locate the bone structures, and output the radiograph with the detected landmarks of the bone structures. The output radiograph containing the detected landmarks may be then forwarded to the trained ROI extraction and segmentation model 114b as input. The trained ROI extraction and segmentation model 114b may process the received radiograph containing the detected landmarks, and automatically extract a region of interest (e.g., a left hip) based on the detected anatomical landmarks by the trained landmark detection model 112b. The trained ROI extraction and segmentation model 114b may further perform fully automated segmentation of the bone structure (e.g., the proximal femur) from the extracted ROI (e.g., ROI of the left hip) and produce a segmentation mask. The ROI and segmentation mask may be then further processed (e.g., augmented) by the ROI extraction and segmentation model 114b before being forwarded to the BMD estimation model 116b for BMD estimation. The BMD estimation model 116b may receive the extracted ROI and segmentation mask and conduct a BMD estimation for the segmented bone structure. Further details regarding the processing of a plain radiograph by the plain radiograph-based BMD estimation unit 103 may refer to the description in FIGS. 3-10.

In some embodiments, besides the trained landmark detection model 112b, ROI extraction and segmentation model 114b, and BMD estimation model 116b configured for the plain radiograph-based BMD estimation, the plain radiograph-based BMD estimation unit 103 may additionally include input and output interfaces (not shown) to communicate with plain radiograph database 104 and/or network 105. Consistent with some embodiments, plain radiograph-based BMD estimation unit 103 may be implemented with hardware (e.g., as disclosed in FIG. 2) specially programmed by software that performs a plain radiograph-based BMD estimation process.

Plain radiograph-based BMD estimation unit 103 may communicate with plain radiograph database 104 to receive one or more plain radiographs. These plain radiographs stored in plain radiograph database 104 may be obtained from any medical image sources (e.g., medical institutes or other resources). These plain radiographs are typically not landmark-labeled or segmented yet. Consistent with the disclosed embodiments, the plain radiographs may be acquired using various imaging modalities, such as Computed Tomography (CT) and X-ray. In some embodiments, plain radiograph database 104 may be an integrated part of plain radiograph-based BMD estimation unit 103, or located on the same site of plain radiograph-based BMD estimation unit 103, such as in a radiotherapy treatment room. For specific detail regarding the processing of the plain radiograph-based BMD estimation unit 103, may refer to descriptions with respect to FIGS. 3-10 in the following descriptions.

Network 105 may provide connections between any of the above-described components in plain radiograph-based BMD estimation system 100. For example, network 105 may be a local area network (LAN), a wireless network, a cloud computing environment (e.g., software as a service, platform as a service, infrastructure as a service), a user-server, a wide area network (WAN), and the like.

Figure 2:
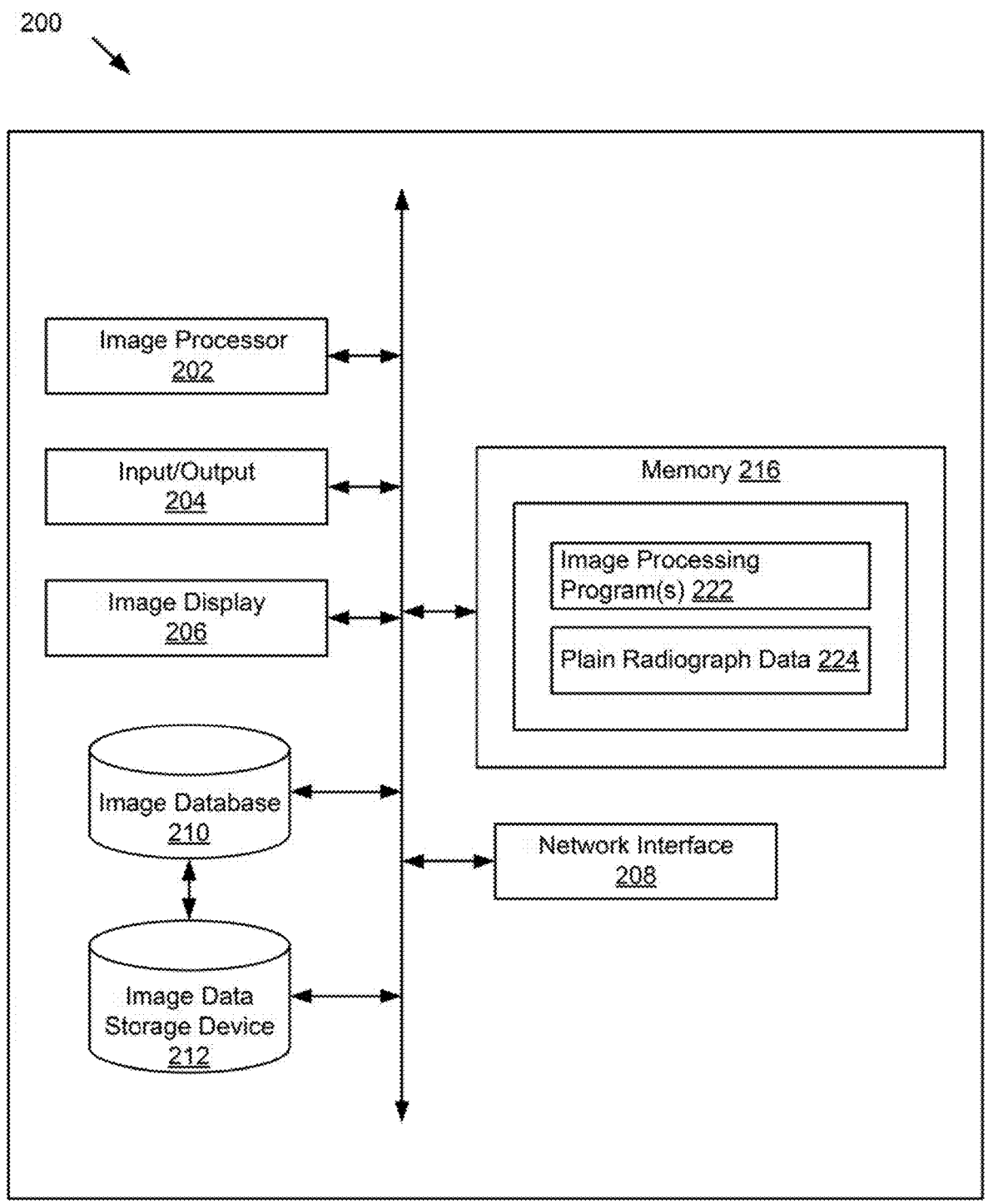
FIG. 2 illustrates an exemplary image processing device, according to some embodiments of the present disclosure.

Referring now to FIG. 2, an exemplary image processing device 200 is provided, according to some embodiments of the present disclosure. The image processing device 200 may be an embodiment of a plain radiograph-based BMD estimation model training unit 102, or a plain radiograph-based BMD estimation unit 103, or a combination of the two. As would be appreciated by those skilled in the art, in some embodiments, image processing device 200 may be a special-purpose computer, or a general-purpose computer. In one example, image processing device 200 may be a computer custom built for hospitals to handle image acquisition and image processing tasks.

As shown in FIG. 2, image processing device 200 may include an image processor 202, an input/output 204, an image display 206, a network interface 208, an image database 210, an image data storage device 212, and a memory 216.

Image processor 202 may be a processing device, including one or more general-purpose processing devices such as a microprocessor, central processing unit (CPU), graphics processing unit (GPU), or the like. More particularly, image processor 202 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Image processor 202 may also be one or more special-purpose processing devices such as an application specific integrated circuit (ASIC), a field programmable gate array (FPGA), a digital signal processor (DSP), a System on a Chip (SoC), or the like. According to some embodiments, image processor 202 may be an NVIDIA Titan V GPU.

Image processor 202 may be communicatively coupled to memory 216 and configured to execute the computer executable instructions or programs stored thereon. Memory 216 may include a Read-Only Memory (ROM), a flash memory, a Random-Access Memory (RAM), a static memory, a non-transitory memory, etc. In some embodiments, memory 216 may store computer executable instructions, such as one or more image processing programs 222, as well as data used or generated while executing image processing programs 222, such as plain radiograph data 224. Image processor 202 may execute image processing programs 222 to implement functionalities of plain radiograph-based BMD estimation model training unit 102 and/or plain radiograph-based BMD estimation unit 103. The image processor 202 may also send/receive plain radiograph data 224 to/from memory 216. For example, image processor 202 may receive training medical image data stored in memory 216. Image processor 202 may also generate intermediate data, such as regions of interest (ROIs), segmentation masks, and send them to memory 216.

The image processing device 200 may optionally include an image database 210, which may include one or both of training image database 101 and plain radiograph database 104. One skilled in the art would appreciate that image database 210 may include a plurality of storage units located either in a central or distributed manner. Image processor 202 may communicate with mage database 210 to read images into memory 216 or store ROIs and segmented images from memory 216 to image database 210.

Image data storage device 212 may be an additional storage available to store data associated with image processing tasks performed by image processor 202. In some embodiments, image data storage device 212 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that causes the machine to perform any one or more of the methodologies of the present disclosure. The term "machine-readable storage medium" shall accordingly be taken to include, but not be limited to, solid-state memories, optical and magnetic media.

Input/output 204 may be configured to allow data to be received and/or transmitted by image processing device 200. Input/output 204 may include one or more digital and/or analog communication devices that allow image processing device 200 to communicate with user or other machines and devices. For example, input/output 204 may include a keyboard and a mouse for a user to provide input.

Image display 206 may be any display device that suitable for displaying the medical images, detected landmarks, extracted ROIs, segmented bone structures, etc. For example, image display 206 may be an LCD, CRT, or LED display.

Network interface 208 may include a network adaptor, a cable connector, a serial connector, a USB connector, a parallel connector, a high-speed data transmission adaptor such as fiber, USB 2.0, thunderbolt, and the like, a wireless network adaptor such as a WiFi adaptor, a telecommunication (3G, 4G/LTE, 5G, and the like) adaptor, and the like. Image processing device 200 may be connected to network 105 through network interface 208.

Image processing programs 222 in memory 216 may include any programs that facilitate image processing. When implemented by image processor 202, image processing programs 222 may allow medical images to be processed in image processing device 200. For instance, image processing programs 222 may include a plain radiograph-based BMD estimation unit 103 for estimating BMDs of medical images. In some embodiments, image processing programs 222 may also include programs for training un-trained plain radiograph-based BMD estimation models 112a, 114a, and/or 116a. Specific functions of these image processing programs 222 are described hereinafter with reference to FIGS. 3-10.

Figure 3:
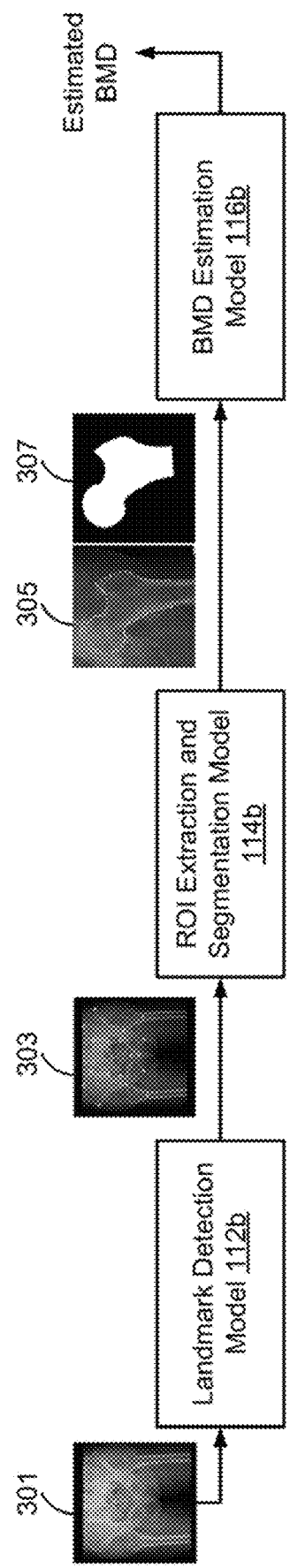
FIG. 3 illustrates an exemplary overview of a plain radiograph-based BMD estimation method, according to some embodiments of the present disclosure.

FIG. 3 illustrates an exemplary overview of a plain radiograph-based BMD estimation method 300 for BMD estimation, according to some embodiments of the present disclosure. Briefly, a plain radiograph received from an image source may be first processed for sample preparation, for example, by grayscaling and resizing to a resolution (e.g., 2,688×2,688 pixels) stored as certain bits (e.g., 12 bits). After sample pre-processing, the plain radiograph 301 may be input into a landmark detection model 112b, to formulate the anatomical landmarks of the bone structures (e.g., pelvis and hips, spines) in the plain radiograph as a graph, and then through topology-based cascaded graph convolutions to robustly and accurately detect anatomical landmarks to locate the target bone structures (e.g., the hips), as shown in radiograph 303 in FIG. 3. The radiograph 303 with detected anatomical landmarks may be forwarded by the landmark detection model 112b to an ROI extraction and segmentation model 114b for target ROI extraction and segmentation mask generation. Specifically, an ROI of a target part (e.g., left hip) may be automatically extracted based on the detected anatomical landmarks. An automated segmentation may be then performed to produce a segmentation mask for the extracted ROI (e.g., hip ROI). The extracted ROI 305 and generated segmentation mask 307 may be then augmented, e.g., by random rotation (−180 to +180 degrees), and subsequently resized to a predefined size (e.g., 192×192 pixels). The ROI 305 may be also augmented by intensity jittering (e.g., varying the brightness from −0.2 to +0.2 and the contrast from −0.2 to 0.2). The augmented ROI and segmentation mask may be used as an input for a BMD estimation model 116b, which may be a regression model based on the deep texture encoding network (Deep-TEN). The BMD estimation model 116b may estimate the BMD for the bone structure based on the BMD value estimated from the target ROI. It is to be noted, FIG. 3 merely provides a brief description of the plain radiograph-based BMD estimation. Detailed descriptions of the plain radiograph-based BMD estimation are provided hereinafter with reference to FIGS. 4-10.

Figure 4:
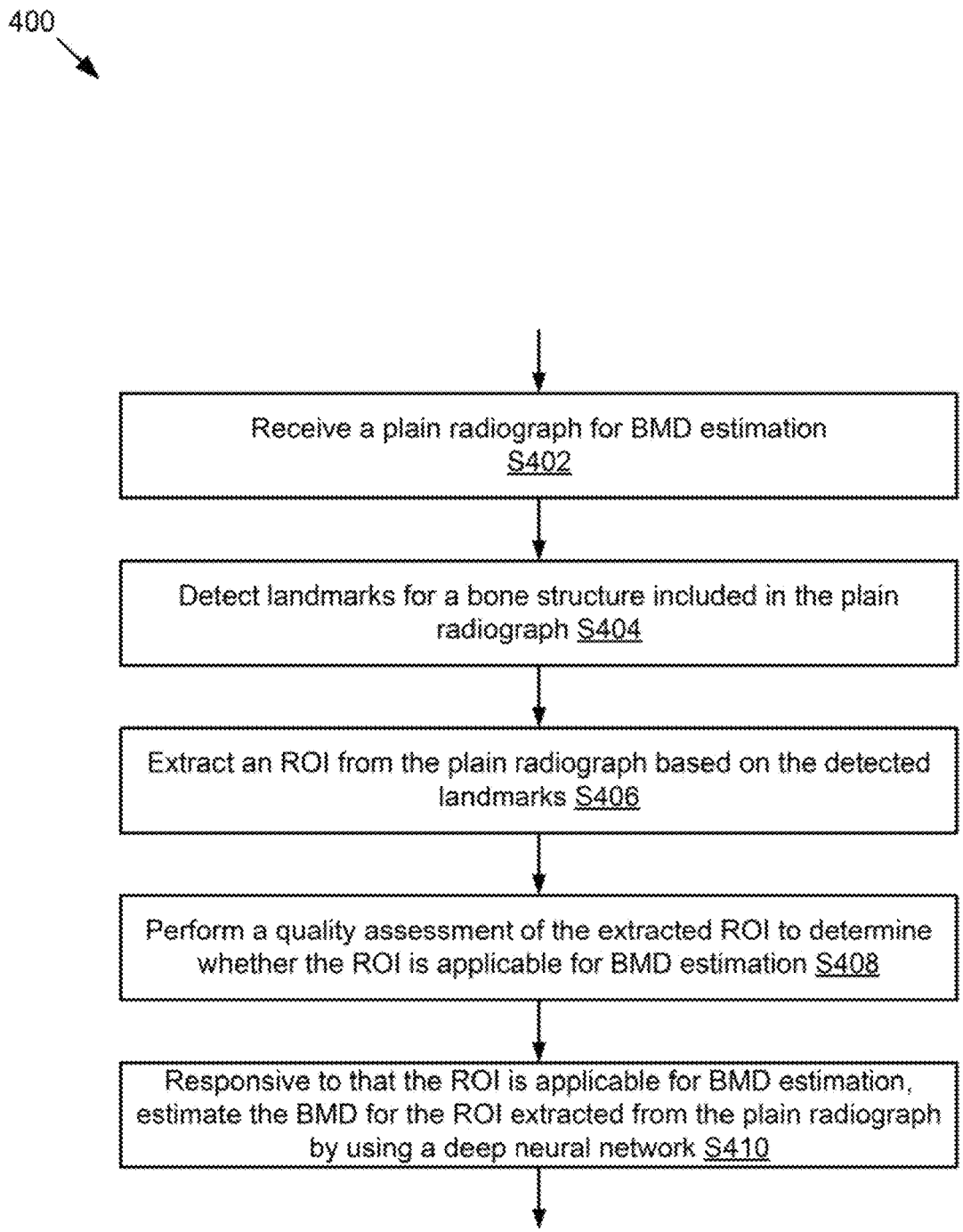
FIG. 4 is a flowchart illustrating an exemplary method for plain radiograph-based BMD estimation, according to some embodiments of the present disclosure.

FIG. 4 is a flowchart of an exemplary method 400 for plain radiograph-based BMD estimation, according to some embodiments of the present disclosure. Consistent with the disclosed embodiments, the exemplary method may be implemented by a plain radiograph-based BMD estimation unit 103.

In S402, the plain radiograph-based BMD estimation unit 103 may receive a plain radiograph for BMD estimation. The plain radiograph may be received as a digital image and may be subject to image processing by the plain radiograph-based BMD estimation unit 103. The received radiograph may be at a size, format, resolution that do not fit the plain radiograph-based BMD estimation unit 103, and thus may be pre-processed first by the plain radiograph-based BMD estimation unit 103. For instance, the plain radiograph-based BMD estimation unit 103 may grayscale and resize the received radiograph to a certain resolution (e.g., a resolution of 2,688×2,688 pixels) stored as a certain resolution (e.g., 12 bits).

In S404, the plain radiograph-based BMD estimation unit 103 may detect landmarks for a bone structure included in the pre-processed radiograph. The landmark detection process may be implemented by the landmark detection model 112b in the plain radiograph-based BMD estimation unit 103. The detected landmark may relate to a bone structure with the received radiograph. For instance, if the received radiograph is a pelvic X-ray, the detected landmarks may relate to pelvis and hip structures. In some embodiments, landmark detection model 112b may be trained with pelvic and hip structures, so as to detect landmarks for similar bone structures. Specific details regarding the automatic landmark detection are provided in FIG. 5.

In S406, the plain radiograph-based BMD estimation unit 103 may extract an ROI for the bone structure from the plain radiograph based on the detected landmarks. For instance, a target hip ROI may be extracted from the pelvic X-ray film. In some embodiments, segmentation may be further processed by the plain radiograph-based BMD estimation unit 103, to automatically segment the target bone structure from the ROI and produce a segmentation mask. In some embodiments, the extracted ROI and segmentation mask may be further augmented, as previously described. Specific details regarding ROI extraction and segmentation are provided in FIGS. 6A-6D.

In S408, the plain radiograph-based BMD estimation unit 103 may perform a quality assessment of the extracted BMD to determine whether the extracted ROI is applicable for BMD estimation. In some embodiments, certain radiograph samples may be not applicable for BMD estimation. For instance, a bone with a fracture, an implant, etc., may be not appropriate for BMD estimation since the fracture and implant and the like may affect the accurate estimation of the BMD. These samples may be excluded for BMD estimation and thus will not be processed further. If a radiograph sample is applicable for BMD estimation, the extraction ROI and generated segmentation mask may be then subject to the BMD estimation. Specific details regarding the ROI quality assessment are provided in FIGS. 7A-7B.

In S410, the plain radiograph-based BMD estimation unit 103 may estimate the BMD for the ROI extracted from the plain radiograph by using a deep neural network. Based on the estimated BMD value of the target ROI, the plain radiograph-based BMD estimation unit 103 may thus provide an estimated BMD value for the target bone structure. The estimated BMD value may be useful for osteoporosis evaluation. Specific details regarding the BMD estimation are provided in FIG. 8.

Figure 5:
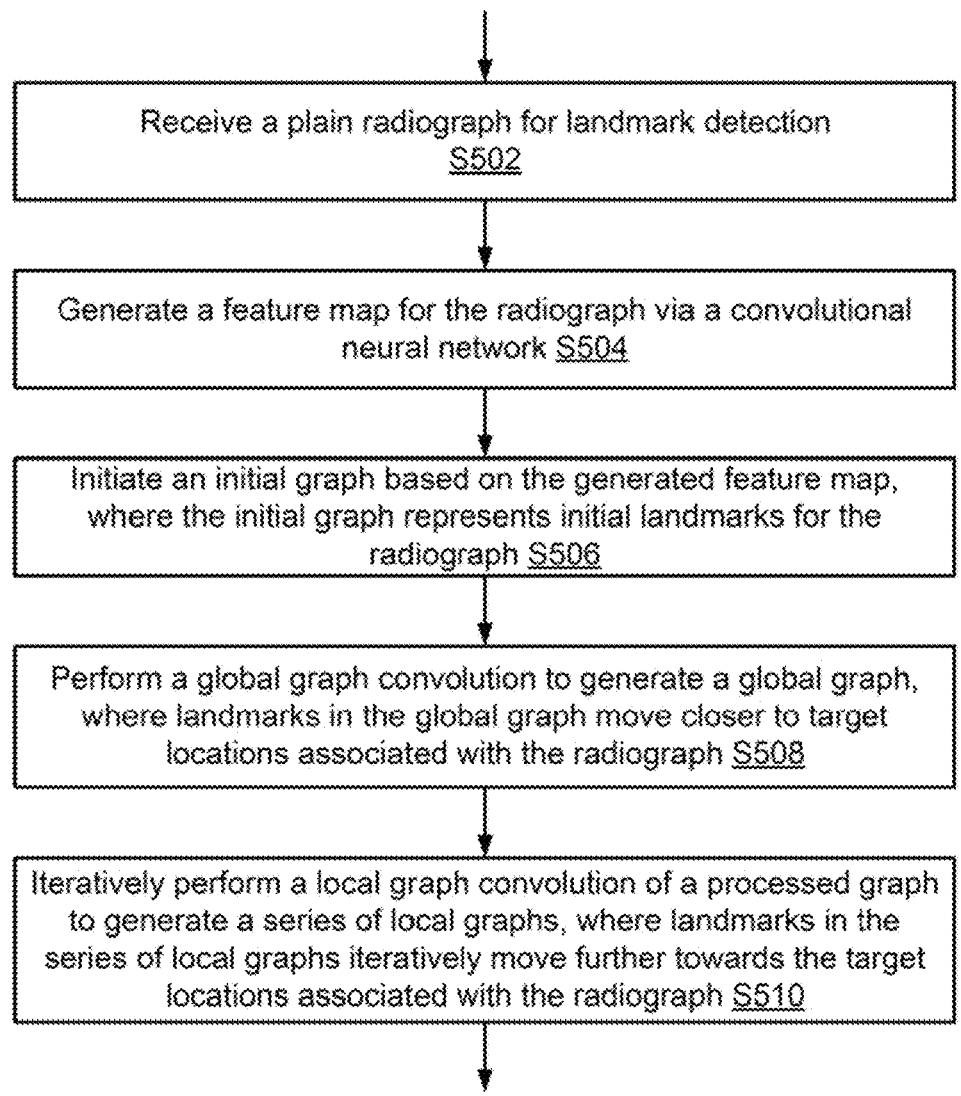
FIG. 5 is a flowchart illustrating an exemplary method for automatically detecting a region of interest from a radiograph, according to some embodiments of the present disclosure.

FIG. 5 is a flowchart of an exemplary method 500 for landmark detection, according to some embodiments of the present disclosure. In some embodiments, the method 500 may be implemented by the landmark detection model 112b in the plain radiograph-based BMD estimation unit 103.

In S502, an input image (e.g., a radiograph) for landmark detection is received, e.g., by landmark detection model 112b. The input image may be a plain radiograph and may be received from a user device, or image processing device, an online source, or from any other resources.

In S504, a feature map may be generated by a backbone network inside the landmark detection model 112b that receives the input image. The backbone network for generating the feature map may be a convolutional neural network (CNN), such as HRNet, ResNet, Stacked Hourglass, among others. According to one embodiment, an HRNet pre-trained on ImageNet may be used as the backbone network to extract visual feature maps, for its parallel multi-resolution fusion mechanism and deep network design which fits the need for both high resolution and semantic feature representation. The last output after fusion from the backbone network (e.g., HRNet) may be extracted as a feature map with a certain dimension.

In S506, an initial graph may be initialized, which represents initial landmarks for the input image (e.g., initial landmarks for a bone structure inside the radiograph). The initial landmarks may take a mean shape of landmarks from training data, which may be radiographs with annotated landmarks for the similar bone structure.

In S508, a global graph convolution is performed to estimate a global transformation to generate a global graph, in which the landmarks are coarsely moved to the targets (i.e., expected landmark locations). The global graph convolution may be performed by a graph convolutional network (GCN) within the landmark detection model 112b, to generate the global graph. In some embodiments, the global graph convolution may be considered as the mechanism of information collection among the neighborhood landmarks (e.g., the coordinates of the mouth landmarks can be somehow inferred from the eyes and nose). A perspective transformation may be applied to transform and reshape the graph containing the initial landmark node coordinates to obtain the aligned landmark coordinates. Here, the aligned landmark coordinates (i.e., the landmarks after the transformation or the transformed landmarks) may represent the coarse movement of the initial landmarks to the targets.

In S510, a local graph convolution may be iteratively performed to generate a series of local graphs, and to estimate local landmark coordinate offsets so as to iteratively move the landmarks toward the targets. Given the transformed landmarks in the global graph from S508, a second graph convolution, i.e., GCN-local, may be applied to further shift the graph iteratively. In some embodiments, GCN-local may employ the same architecture as GCN-global. The updated landmark coordinates in each generated local graph may represent a closer movement to the targets after each iteration of GCN-local transformation. Through one or more iterations of GCN-local transformation, the updated coordinates may eventually move to, or at least close enough to, the target locations, thereby allowing the landmarks of the bone structure (e.g. pelvis and hips) to be detected. Consistent with the disclosed embodiments, the detected landmarks may be forwarded to the ROI extraction and segmentation model 114b in the plain radiograph-based BMD estimation unit 103 for ROI extraction and segmentation.

Figure 6A:
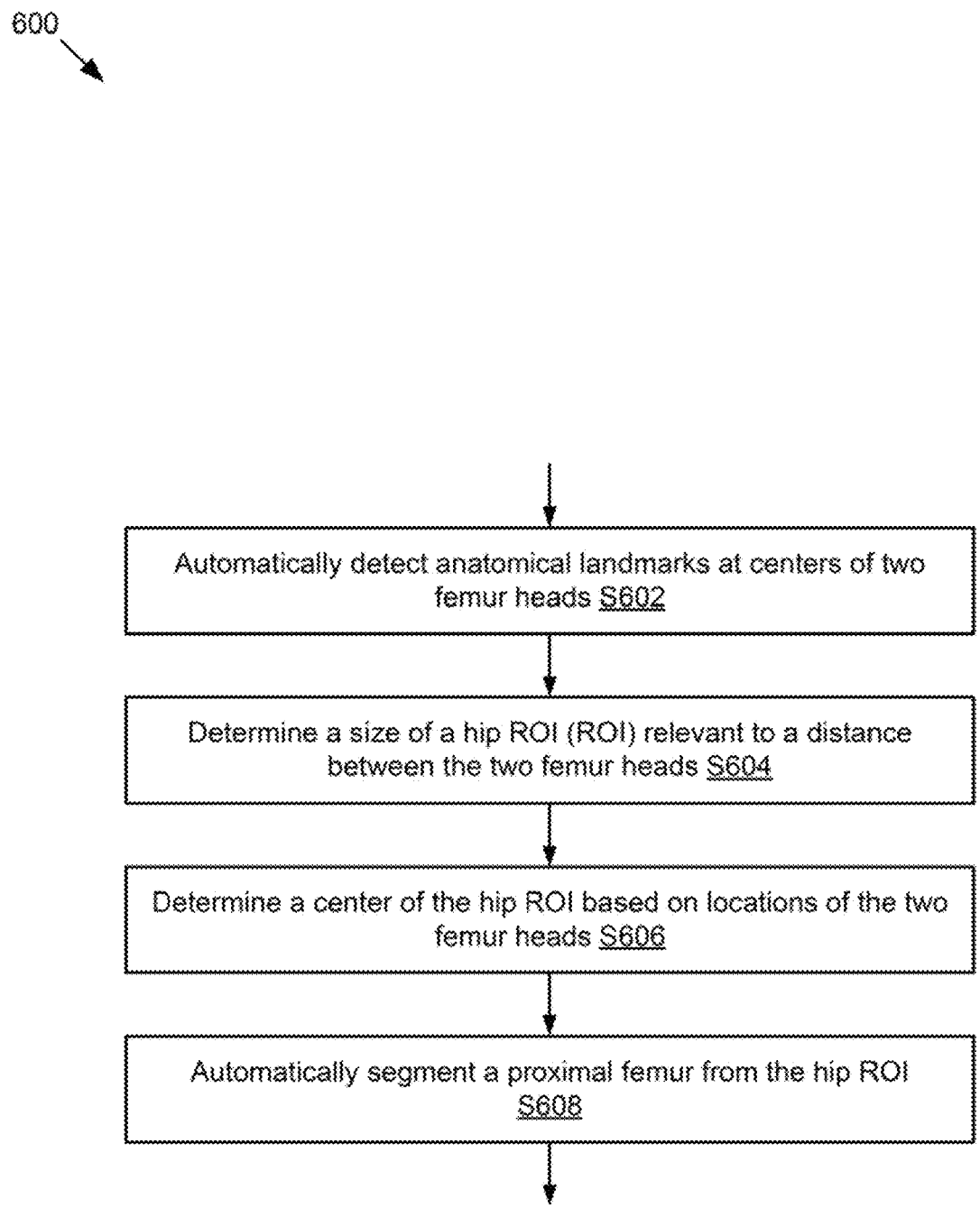
FIG. 6A is a flowchart of an exemplary method for ROI extraction and segmentation, according to some embodiments of the present disclosure.
Figure 6B:
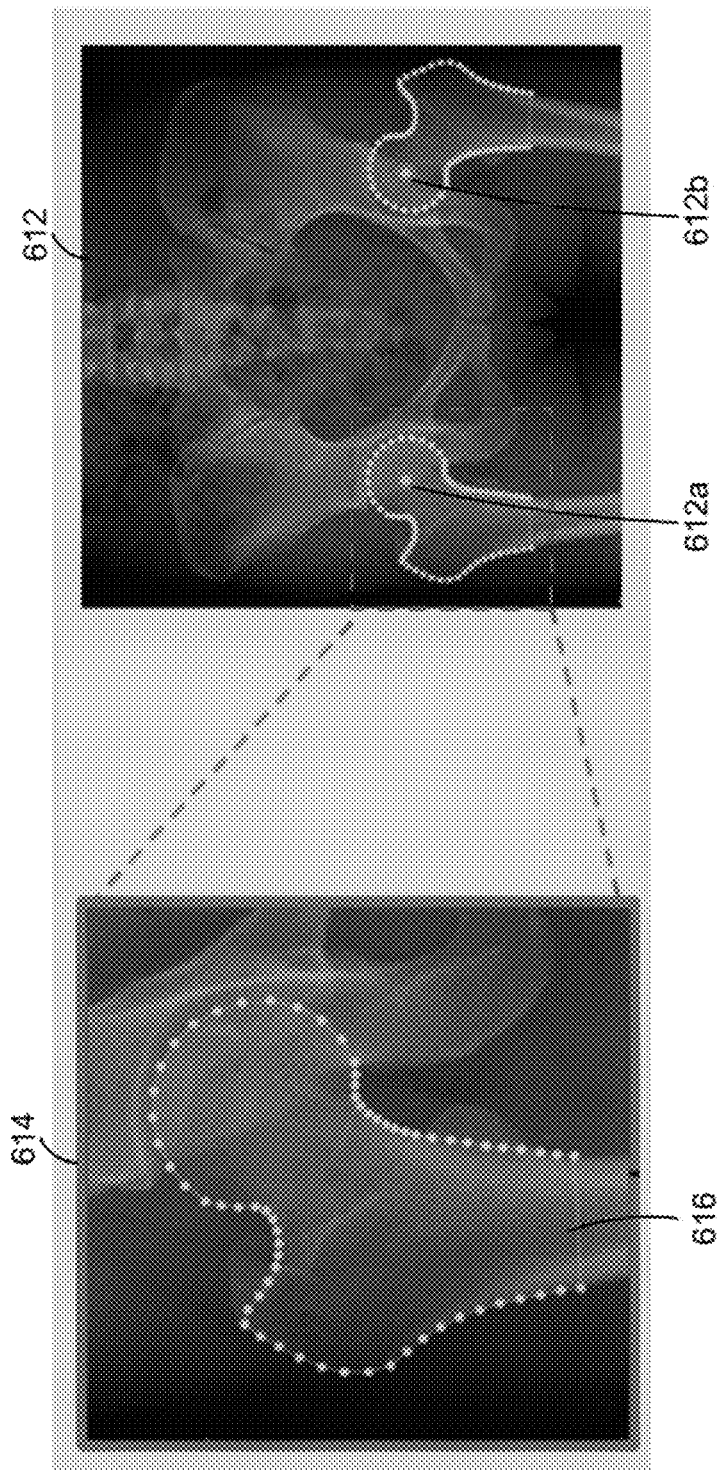
FIG. 6B illustrates an exemplary hip ROI and hip segmentation, according to some embodiments of the present disclosure.

FIG. 6A is a flowchart of an exemplary method 600 for ROI extraction and segmentation, according to some embodiments of the present disclosure. FIG. 6B illustrates an exemplary hip ROI and segmentation, according to some embodiments of the present disclosure. In some embodiments, the exemplary method 600 for ROI extraction and segmentation may be performed by the ROI extraction and segmentation model 114b in the plain radiograph-based BMD estimation unit 103.

In Method 600, a target ROI region (e.g., a hip ROI 614) covering a target bone structure (i.e., hip) may be identified by the ROI extraction and segmentation model 114b. Specifically, in S602, the ROI extraction and segmentation model 114b may automatically detect anatomical landmarks at centers of two femur heads (e.g. landmarks 612a and 612b at the centers of the two femur heads, as shown in FIG. 6B). The centers of two femur heads may be identified based on the landmarks detected for the hip structure by the landmark detection model 112b. For instance, the landmark detection model 112b may generate a feature map for the plain radiograph via a convolutional neural network, and initialize an initial graph based on the generated feature map, where the initial graph represents initial landmarks of the femur head (and optionally other portions of the hip structure included in the plain radiograph). Next, the landmark detection model 112b may perform a global graph convolution of the initial graph to generate a global graph, where the landmarks in the global graph move closer to target locations associated with the femur head. Further, the landmark detection model 112b may iteratively perform a local graph convolution of the global graph to generate a series of local graphs, where landmarks in the series of local graphs iteratively move further towards the target locations associated with the femur head. In this way, the landmarks for the femur head may be detected. It is to be noted that other hip structures (e.g., greater trochanter and lesser trochanter) included in the plain radiograph may be also detected, based on the configuration of the landmark detection model 112b (e.g., how the landmark detection model is trained).

In S604, the ROI extraction and segmentation model 114b may determine the size of the target ROI (e.g., hip ROI 614, as illustrated in FIG. 6B) relevant to a distance between the two femur heads. In some embodiments, when the distance between the two femur heads is determined, the overall size of the pelvic and hip structure may be determined, at least approximately, since the ratio of the distance between the two femur heads to the size of the overall pelvic and hip structure does not really change much from person to person. After determining the size of the overall pelvic and hip structure, the size of the target hip ROI covering the hip structure (e.g., left hip), including the femur head, the greater trochanter, and the lesser trochanter, may be also determined, as shown in ROI 614 in FIG. 6B.

In S606, the center of the target hip ROI may be further determined based on the locations of the detected femur heads. Since the locations of the detected femur heads may also allow inferring the size and locations of the femur head, the greater trochanter, and the lesser trochanter, it is possible to determine the location of the hip target ROI based on the locations of the detected femur heads. After determining the size and location of the target hip ROI, the target ROI may be then determined correspondingly. For instance, the determined ROI may be a rectangular region containing a femur head, a greater trochanter, and a lesser trochanter (e.g., ROI 614 as illustrated in FIG. 6B).

It is to be noted that the above steps S602-S606 merely provide one exemplary method for extracting the hip ROI from the plain radiograph. Other approaches for extracting the hip ROI may be also possible and thus are contemplated. For instance, according to one embodiment, the ROI extraction and segmentation model 114b may first segment the femur head, the greater trochanter, and the lesser trochanter based on the detected landmarks for the hip, and then determine a size and a location of the target hip ROI that covers the detected femur head, the greater trochanter, and the lesser trochanter.

In S608, segmentation may be further performed to segment the proximal femur from the hip ROI and produce a segmentation mask. To achieve this, the disclosed ROI extraction and segmentation model 114b may further include a contour transformer network (CTN), which is a one-shot anatomy segmentor including a naturally built-in human-in-the-loop mechanism. The CTN network in the disclosed ROI extraction and segmentation model 114b may be trained to fit a contour to the object boundary by learning from one labeled exemplar. It takes the exemplar and an unlabeled image as input, and estimates a contour that has similar contour features with the exemplar. Therefore, even if there are not enough manual image segmentation labels and masks to train an image segmentation model, just one sampler (e.g., one hip image with segmentation label and mask) may be obtained to train the CTN network included in the ROI extraction and segmentation model 114a to obtain the trained ROI extraction and segmentation model 114b (it is to be noted that the network for ROI extraction included in the ROI extraction and segmentation model 114a may be trained differently with a different set of training samples).

In some embodiments, the CTN network for segmentation may be generated through the following process. First, an annotated image (e.g., an annotated hip image) is provided, where the annotated image includes an annotated contour (e.g., for a proximal femur). Next, a plurality of unannotated images are provided, and the annotated image is overlaid to each of the plurality of unannotated images to obtain a plurality of image overlays. Next, the plurality of image overlays are fed to a contour encoder to obtain a plurality of first-processed image overlays, where one of the plurality of first-processed image overlays shows a first output contour with a first vertices offset relative to the annotated contour of the annotated image. Next, the plurality of first-processed image overlays are fed to a contour tuner to obtain a plurality of second-processed image overlays, where the one of the plurality of first-processed image overlays corresponds to one of the plurality of second-processed image overlays, and where the one of the plurality of second-processed image overlays shows a second output contour with a second vertices offset smaller than the first vertices offset. Through this process, the CTN network may be trained, which is then further included in the ROI extraction and segmentation model 114*b* for segmenting the images containing the hip structures, for example, for segmenting a proximal femur from the hip ROI and for producing a segmentation mask for the segmented proximal femur (e.g., femur segmentation 616 as illustrated in FIG. 6B).

In some embodiments, the extracted ROI and segmentation task may be further augmented. For instance, the hip ROI and segmentation mask may be augmented by random rotation (−180 to +180 degrees) and subsequently resized to a certain size (e.g., 192×192 pixels). The ROI may be further augmented by intensity jittering (varying the brightness from −0.2 to +0.2 and the contrast from −0.2 to 0.2). The processed ROI and segmentation mask may be then used as the input of the BMD estimation model 116*b*, as further described in FIG. 8.

Figure 6C:
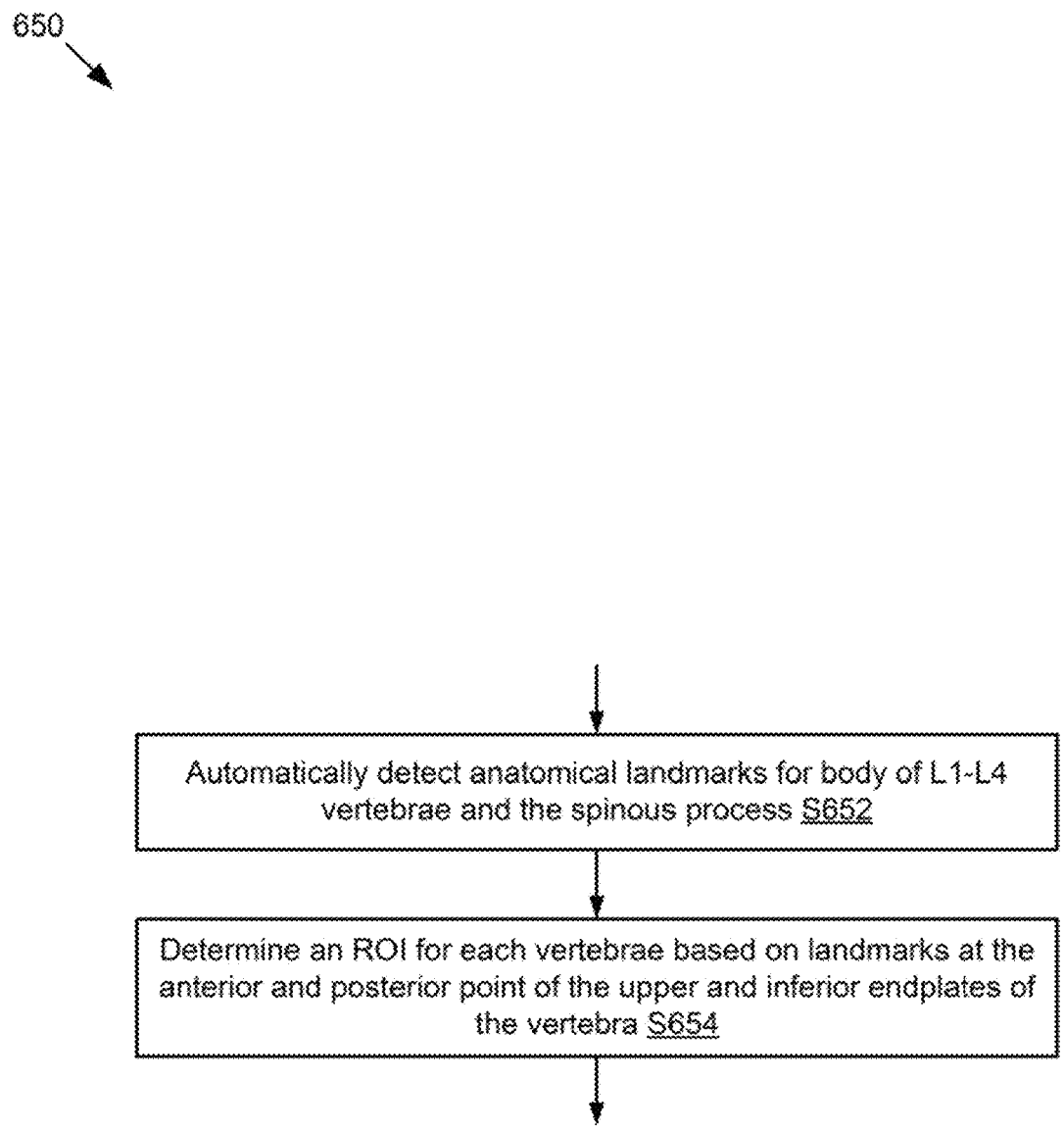
FIG. 6C is a flowchart of another exemplary method for ROI extraction and segmentation, according to some embodiments of the present disclosure.
Figure 6D:
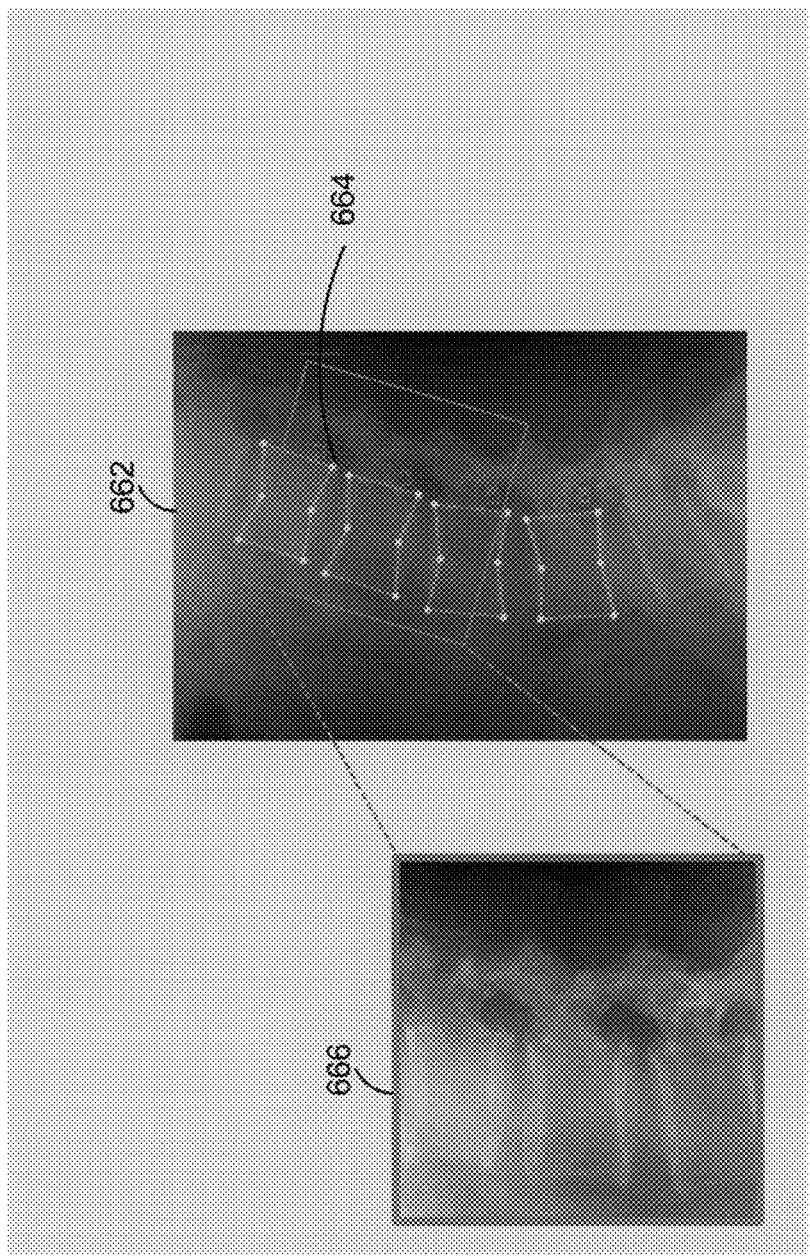
FIG. 6D illustrates an exemplary vertebra ROI and segmentation, according to some embodiments of the present disclosure.

FIGS. 6A-6B merely provide an exemplary method for ROI extraction and segmentation for one specific bone structure, that is, a hip structure. In some embodiments, the disclosed methods may be also applied to other bone structures, as described in the next for vertebrae ROI and segmentation. FIG. 6C is a flowchart of another exemplary method 650 for ROI extraction and segmentation, according to some embodiments of the present disclosure. FIG. 6D illustrates an exemplary vertebra ROI and segmentation, according to some embodiments of the present disclosure.

In Method 650, a target ROI region (e.g., a vertebrae ROI 666) covering one of the vertebrae L1-L4 may be identified by the ROI extraction and segmentation model 114*b*. Briefly, in S652, anatomical landmarks for the body of L1-L4 vertebrae and the spinous process may be automatically detected. The anatomical landmarks may be detected by the landmark detection model 112*b* as previously described. In S654, the detected landmarks may then allow a determination of a vertebrae ROI for each vertebra of L1-L4 based on the landmarks at the anterior and posterior points of the upper and inferior endplates of the vertebra. The ROI extraction and segmentation model 114*b* may be trained with annotated spine samples instead of pelvic and hip samples. The ROI extraction and segmentation model 114*b* trained with the spine samples may be then fed with detected landmarks for spine samples, to extract an ROI vertebra for each vertebra and to generate a segmentation mask for each vertebra.

For instance, as illustrated in FIG. 6D, an x-ray image 662 may be subject to the landmark detection model 112*b* to automatically detect landmarks 664, as illustrated in the figure. These landmarks 664 may allow extraction of a vertebrae ROI 666 for L2 vertebrae. As illustrated in FIG. 6D, the extracted vertebra ROI 666 may include a rectangular region containing the body of the vertebra and the spinous process. In some embodiments, the vertebra ROI 666 may be just defined based on four landmarks at the anterior and posterior points of the upper and inferior endplates of the vertebra. The four landmarks may be selected from six landmarks detected from a landmark detection process. The six landmarks may include landmarks of an anterior point, a middle point, and a posterior point of upper and inferior endplates of a vertebra, as illustrated in FIG. 6D. The six landmarks may be detected by the landmark detection model 112*b* trained with lateral spine X-ray images containing one (e.g., L2 vertebra) or more of L1-L4 vertebrae. Briefly, the as-trained landmark detection model 112*b* may generate a feature map for the plain lateral spine X-ray via a convolutional neural network, and initialize an initial graph based on the generated feature map, where the initial graph represents initial landmarks of an anterior point, a middle point, and a posterior point of upper and inferior endplates of one (e.g., L2 vertebra) or more of L1-L4 vertebrae. The as-trained landmark detection model 112*b* may perform a global graph convolution of the initial graph to generate a global graph, where landmarks in the global graph move closer to target locations associated with the anterior point, the middle point, and the posterior point of the upper and inferior endplates of the one or more of L1-L4 vertebrae. The as-trained landmark detection model 112*b* may further iteratively perform a local graph convolution of the global graph to generate a series of local graphs, where the landmarks in the series of local graphs iteratively move further towards the target locations associated with the anterior point, the middle point, and the posterior point of the upper and inferior endplates of the one or more of L1-L4 vertebrae. In this way, six landmarks may be detected for a vertebra, among which four landmarks (e.g., anterior point and posterior point of upper and inferior endplates of the vertebra) for extracting the vertebra ROI may be identified and used for the vertebra ROI extraction. It is to be noted that, in some embodiments, only four landmarks (e.g., anterior point and posterior point of upper and inferior endplates of a vertebra) are detected and directly used for extracting the vertebra ROI.

In some embodiments, the segmentation may be further processed from each vertebrae ROI to produce a segmentation mask for each vertebra. In some embodiments, the extracted vertebrae ROI and generated segmentation mask may be further augmented, in a process similar to the augmentation process described above with respect to the hip ROI and segmentation mask. The augmented vertebra ROI and segmentation mask may be subject to the BMD estimation by the BMD estimation model 116*b*, as further described in FIG. 8.

In some embodiments, before being forwarded to the BMD estimation model 116*b* for BMD estimation, the extracted ROI for hips or vertebra may be further assessed for their applicability for BMD estimation, as further described below. Accordingly, in some embodiments, the disclosed plain radiograph-based BMD estimation unit 103 may further include an ROI assessment module (not shown FIG. 1). The ROI assessment module may assess the quality of each extracted ROI.

Figure 7A:
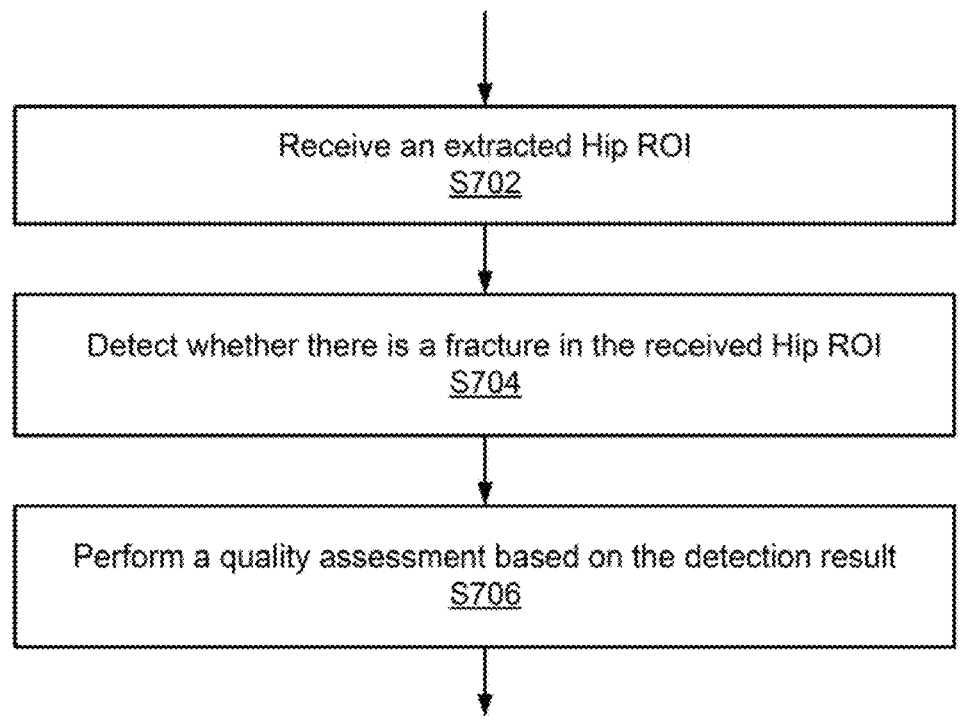
FIG. 7A is a flowchart of an exemplary method for quality assessment of an extracted hip ROI, according to some embodiments of the present disclosure.

FIG. 7A is a flowchart of an exemplary method 700 for quality assessment of an extracted hip ROI, according to some embodiments of the present disclosure. In S702, the extracted ROI may be received by the ROI assessment module. The extracted ROI may be identified to be a hip ROI or a vertebra based on certain information of each ROI, e.g., based on the size and shape of each ROI. If it is determined that the received ROI is a hip ROI, the ROI assessment module may detect whether there is a fracture in the extracted ROI in S704.

In some embodiments, different mechanisms may be applied to identify a fracture from a hip ROI. According to one example, an anatomy-aware Siamese network (AASN) may be included in the ROI assessment module to exploit Semantic asymmetry for accurate pelvis fracture detection in an X-ray image. The AASN may be built upon a Siamese network enhanced with a spatial transformer layer to holistically analyze symmetric image features. Image features are spatially formatted to encode bilaterally symmetric anatomies. A new contrastive feature learning component in the Siamese network may be designed to optimize the deep image features being more salient corresponding to the underlying semantic asymmetries (caused by pelvic fracture occurrences).

In some embodiments, to allow the AASN network to identify fracture or any other anatomical abnormalities, a radiograph may be pre-processed to produce an input image, a flipped image, and a spatial alignment transformation corresponding to the input image and the flipped image. Siamese encoding may be then performed on the input image to produce an encoded input feature map, and on the flipped image to produce an encoded flipped feature map. Next, a feature alignment may be performed by using the spatial alignment transformation on the encoded flipped feature map to produce an encoded symmetric feature map. The encoded input feature map and the encoded symmetric feature map may be then processed, to generate a diagnostic result indicating the presence and locations of anatomical abnormalities in the received radiograph if there are any. For instance, the diagnostic result may indicate whether there is a hip fracture in the extracted hip ROI. In some embodiments, if there are anatomical abnormalities other than hip structure, the AASN network may also identify such anatomical abnormalities in the diagnostic result.

Returning to FIG. 7A, in S706, the ROI assessment module may perform a quality assessment based on the diagnostic result. For instance, if there is a fracture detected in the extracted hip ROI, the extracted ROI may be not applicable for BMD estimation. If there is no fracture in the extracted hip ROI, the hip ROI may be then forwarded to the BMD estimation model 116b for BMD estimation. In some embodiments, the factors or parameters used to assess vertebra ROI may be different from those used to assess hip ROI.

Figure 7B:
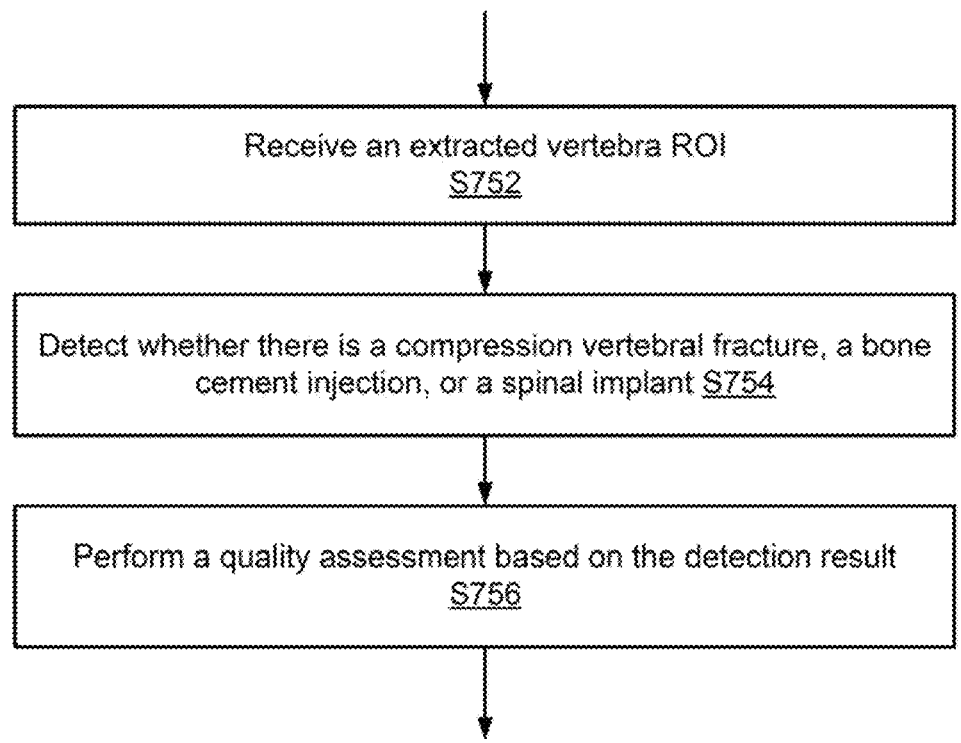
FIG. 7B is a flowchart of an exemplary method for quality assessment of an extracted vertebra ROI, according to some embodiments of the present disclosure.

FIG. 7B is a flowchart of an exemplary method 750 for quality assessment of an extracted vertebra ROI, according to some embodiments of the present disclosure. In S752, a vertebra ROI is received by the ROI assessment module. In S754, the ROI assessment module may detect whether there is a compression vertebral fracture (VCF), a bone cement injection, a spinal implant, or any other anatomical abnormalities. In some embodiments, six-point morphometry criteria based on six landmarks at the anterior, middle, and posterior points of the upper and inferior endplates of the vertebra may be used to detect whether there is a VCF. The six landmarks may be detected by the landmark detection model 112b. The detection of the six landmarks may be similar to the above description for the detection of six landmarks for vertebra ROI extraction, details of which are not repeated here. In some embodiments, a neural network trained for VCF, bone cement injection, spinal implants, or the like, may be trained and included in the ROI assessment module, to allow detection of a VCF, a bone cement injection, or a spinal implant in the target ROI.

In S756, a quality assessment may be then conducted to assess whether the extracted vertebra ROI is applicable for BMD evaluation. If there is any VCF, bone cement injection, or spinal implant, the extracted vertebra ROI may be not applicable for BMD estimation. However, if there is no VCF, bone cement injection, or spinal implant, the extracted vertebra ROI may be forwarded to the BMD estimation model 116b for BMD estimation, as further described hereinafter.

Figure 8:
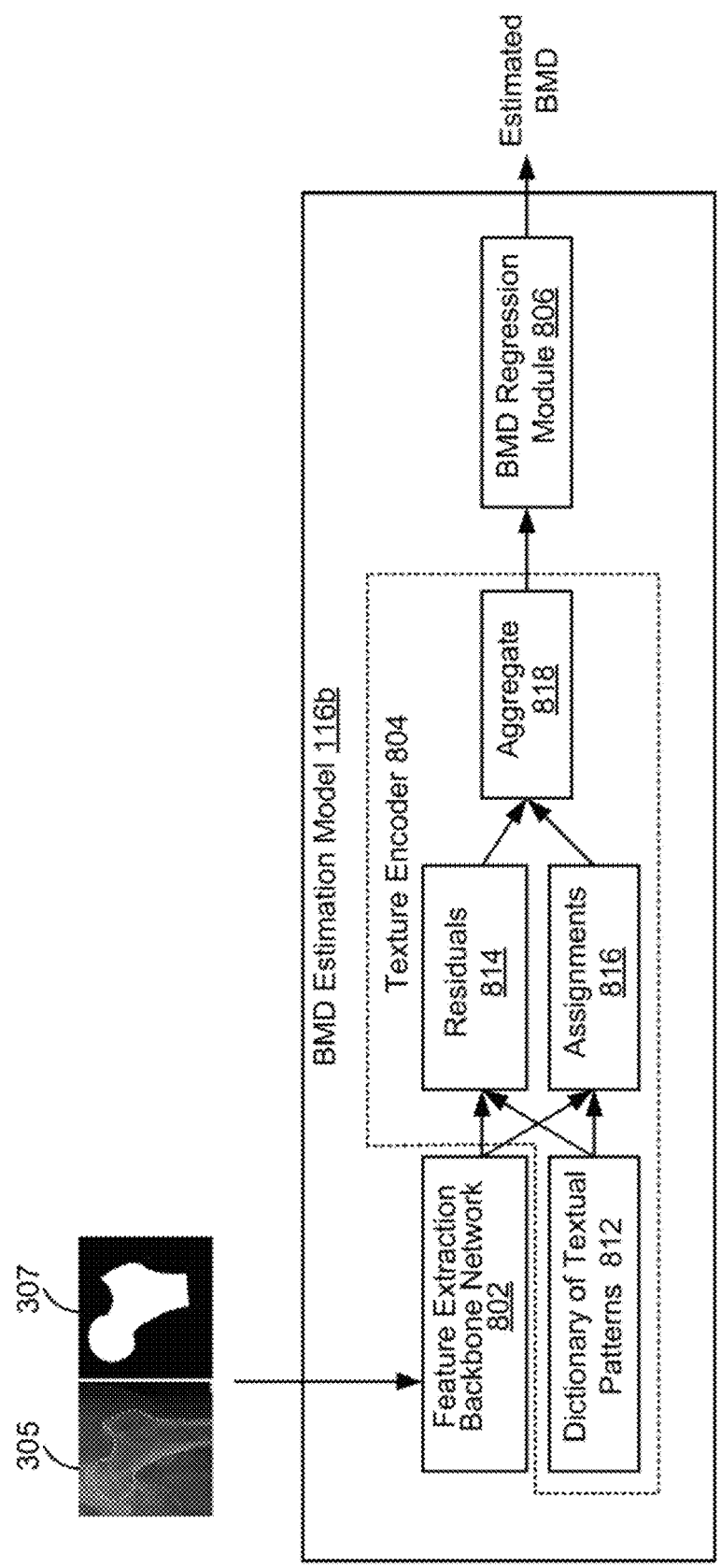
FIG. 8 illustrates a schematic diagram of an exemplary BMD estimation model, according to some embodiments of the present disclosure.

FIG. 8 illustrates a schematic diagram of an exemplary BMD estimation model, according to some embodiments of the present disclosure. As illustrated, the exemplary BMD estimation model 116b may include a feature extraction backbone network 802, a texture encoder 804, and a BMD regression module 806.

Consistent with the disclosed embodiments, the BMD estimation model 116b may be a deep learning algorithm developed based on the Deep-TEN network to extract bone texture features from ROIs. The algorithm may be based on a CNN, which consists of many interconnected processing units (neurons) organized in layers. Each neuron may perform only a simple calculation, but networks with sufficient neurons and layer depths offer sophisticated calculations that can support complicated functions such as image processing. The adopted Deep TEN model may use a pre-trained 18-layer residual backbone network (ResNet18) 802 to extract features (mathematical representations) of local image patterns. The features of image patterns inside the segmented bone structure (e.g., the proximal femur or vertebra) may be then extracted, which contain the textural information of the bone structure included in the respective ROI. The extracted features may be further processed using a texture encoding operator (e.g., texture encoder 804) to obtain encoded feature representation of the bone texture. The texture encoder 804 may automatically learn a dictionary 812 of encodings that are corresponding to different representative textual patterns. Residuals 814 may be calculated by the pairwise difference between texture descriptors output from the feature extraction backbone network 802 and the codewords of the dictionary 812. Meanwhile, weights (i.e., assignments 816) may be assigned based on the pairwise distance between the texture descriptors and the codewords. Eventually, the residual vectors 814 are aggregated with the assigned weights 816. The aggregated texture descriptor 818 may be then processed by a fully-connected layer (i.e., BMD regression module 806) to estimate the BMD.

FIGS. 5-8 provide some general descriptions of the functions of different models or modules in the plain radiograph-based BMD estimation unit 103. However, it is to be noted that the disclosed plain radiograph-based BMD estimation unit 103 is not limited to such functions. In some embodiments, the disclosed plain radiograph-based BMD estimation unit 103 may include fewer or more functions than those described in FIGS. 5-8. Further details regarding how to use the disclosed plain radiograph-based BMD estimation unit 103 to estimate hip and spinal BMDs are provided hereinafter.

Figure 9:
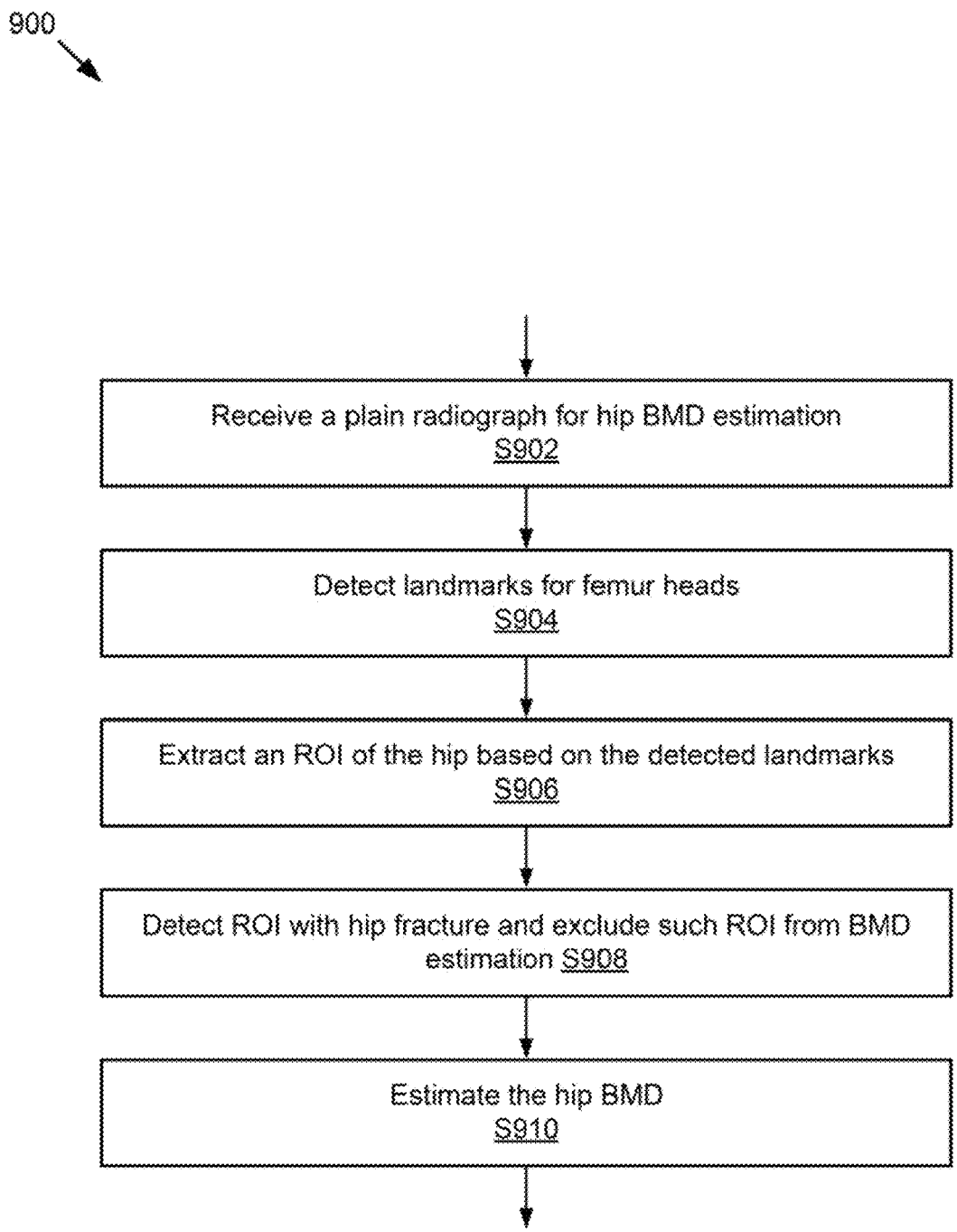
FIG. 9 is a flowchart of an exemplary method for femur BMD estimation, according to some embodiments of the present disclosure.

FIG. 9 is a flowchart of an exemplary method 900 for femur BMD estimation, according to some embodiments of the present disclosure. In S902, a plain radiograph for femur BMD estimation is received (e.g., by the plain radiograph-based BMD estimation unit 103). The plain radiograph may be an anteroposterior pelvic X-ray image of a hip of a human. The plain radiograph may be pre-processed, e.g., grayscaled or resized. In S904, the processed radiograph may be detected for landmarks for the bone structures (e.g., pelvic and hip) included in the plain radiograph. In S906, a hip ROI may be extracted based on the detected landmarks. In some embodiments, the proximal femur may be further segmented from the hip ROI and a segmentation mask for the proximal femur is then produced. In some embodiments, the hip ROI and the corresponding segmentation mask may be further augmented. In S908, the detected ROI is subject to the detection of bone fracture or any other anatomical abnormalities included in the radiograph. If there is no fracture or anatomical abnormality, in S910, the extracted ROI and the segmentation task may be subject to the BMD estimation, to get an estimated BMD value for the hip ROI, which may be considered as the femur BMD useful for osteoporosis diagnosis.

Figure 10:
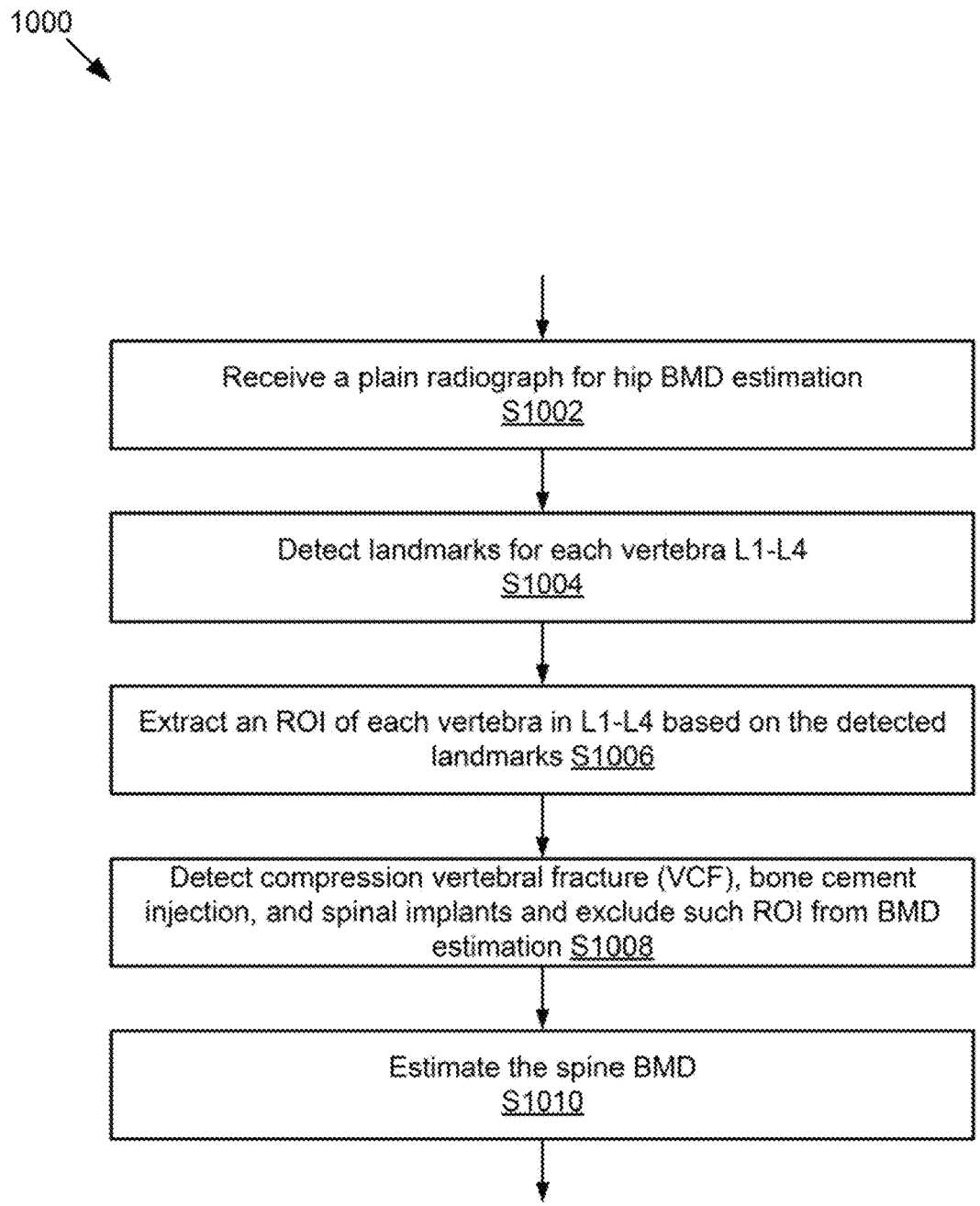
FIG. 10 is a flowchart of an exemplary method for vertebra BMD estimation, according to some embodiments of the present disclosure.

FIG. 10 is a flowchart of an exemplary method 1000 for vertebra BMD estimation, according to some embodiments of the present disclosure. In S1002, a plain radiograph for vertebra BMD estimation is received (e.g., by the plain radiograph-based BMD estimation unit 103). The plain radiograph may be a lateral spine X-ray image for L1-L4 vertebrae of a human. The plain radiograph may be pre-processed, e.g., grayscaled or resized. In S1004, the processed radiograph may be detected for landmarks for the spine structure (e.g., vertebrae L1-L4) included in the radiograph. In S1006, a vertebra ROI may be extracted based on the detected landmarks. In some embodiments, a specific vertebra (e.g., for vertebra L2) may be segmented from the vertebra ROI and a segmentation mask for the corresponding vertebra is then produced. In some embodiments, the vertebra ROI and the corresponding segmentation mask may be further augmented. In S1008, the detected ROI is subject to detection of CVF, bone cement injection, a spinal implant, or any other anatomical abnormalities included in the radiograph. If there is no such anatomical abnormality, in S1010, the extracted ROI and the segmentation task may be subject to the BMD estimation, to get an estimated BMD value for the vertebra ROI. In this way, the BMD for a hip or vertebra ROI may be estimated by the disclosed plain radiograph-based BMD estimation unit 103.

In some embodiments, to verify the effectiveness and accuracy of the disclosed plain radiograph-based BMD estimation tool, some training and testing samples may be collected to train and test the disclosed plain radiograph-based BMD estimation unit 103.

Table 1 shows the characteristics of the samples in the training and testing sets. The testing dataset consisted of 360 individuals, of whom 291 (80.8%) are women, and 69 (19.2%) are men (mean age, 70.7±11.7 years). The demographics, weight, height, measured BMD, T score, and Fracture Risk Assessment Tool (FRAX™) risk scores of the patients in the testing set are similar to those in the training set.

TABLE 1

| | Training N = 1435 | Testing N = 360 | P-value |
|---|---|---|---|
| Age | 69.4 ± 13.3 | 70.7 ± 11.7 | 0.064 |
| Gender | | | |
| Male | 262 (18.3%) | 69 (19.2%) | 0.691 |
| Female | 1173 (81.7%) | 291 (80.8%) | |
| Weight | 58.2 ± 11.5 | 58.5 ± 11.7 | 0.751 |
| Height | 155.7 ± 10.0 | 155.9 ± 7.5 | 0.620 |
| BMD of Hip | 0.69 ± 0.16 | 0.68 ± 0.16 | 0.818 |
| T score | −2.45 ± 1.30 | −2.50 ± 1.29 | 0.478 |
| FRAX ™ - major fracture risk (%) | 3.86 ± 2.36 | 3.73 ± 2.39 | 0.451 |
| FRAX ™ - Hip fracture (%) | 1.27 ± 1.51 | 1.21 ± 1.58 | 0.587 |

Figure 11:
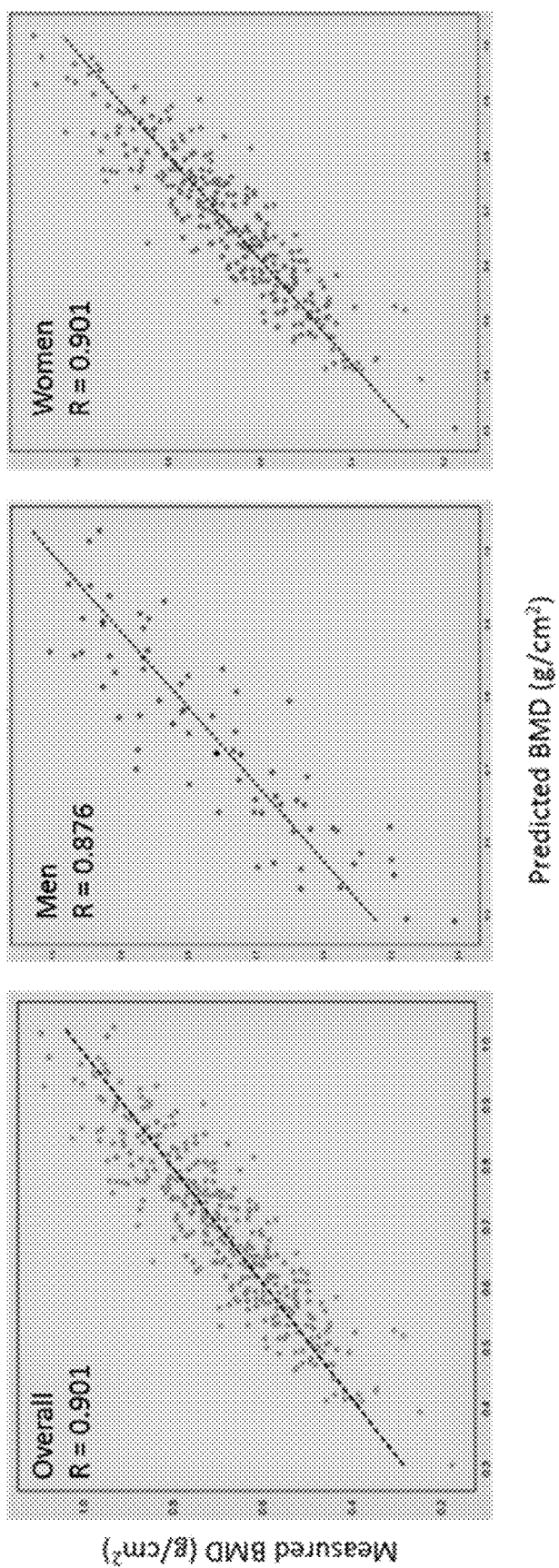
FIG. 11 illustrates exemplary scatter plots of BMDs measured by DXA and estimated by plain radiograph-based BMD estimation method, according to some embodiments of the present disclosure.

FIG. 11 illustrates exemplary scatter plots of BMDs measured by DXA and estimated by plain radiograph-based BMD estimation method, according to some embodiments of the present disclosure. From the figure, it can be seen that the BMD values estimated by the plain radiograph-based BMD estimation method match pretty well with the BMD values measured by DXA. The correlation between the measured and estimated BMD values is 0.876 for men and 0.901 for women. The mean BMD estimated by the plain radiograph-based BMD estimation method is 0.68±0.16 g/cm$^2$, while the mean BMD measured by DXA is 0.69±0.14 g/cm$^2$. The difference is not statistically significant (p=0.800).

Table 2 shows a comparison between the T scores and FRAX™ risk scores for major fracture and hip fracture risks based on the BMD value measured by DXA or estimated by the plain radiograph-based BMD estimation method, respectively. The mean FRAX™ 10-year major fracture risk does not differ significantly between the scores based on the estimated (3.51%) or measured BMD (3.73%, p=0.280). The 10-year probability of hip fracture is slightly lower when calculated from the estimated score (1.05%) than when calculated from the measured score (1.21%, p=0.218).

TABLE 2

| | Measured BMD by DXA | Estimated BMD by plain radiograph-based BMD estimation method | P-value |
|---|---|---|---|
| BMD | 0.68 ± 0.16 | 0.69 ± 0.14 | 0.800 |
| T-score | −2.50 ± 1.29 | −2.51 ± 1.11 | 0.937 |
| FRAX ™ - Major fracture risk (%) | 3.73 ± 2.39 | 3.51 ± 1.86 | 0.280 |
| FRAX ™ - Hip fracture (%) | 1.21 ± 1.58 | 1.05 ± 1.07 | 0.218 |

Next, the ability and accuracy of the model to detect osteoporosis are also assessed. The sensitivity and specificity scores are 0.86 (0.81-0.91) and 0.89 (0.83-0.93), respectively, and the positive and negative estimative values are 0.90 (0.85-0.93) and 0.85 (0.80-0.89), respectively.

From the foregoing qualitative data, it can be seen that the disclosed plain radiograph-based BMD estimation method achieves BMD values similar to those measured by DXA. Furthermore, the plain radiograph-based BMD estimation method performs well on both important tasks of osteoporosis identification and FRAX™ score estimation. Based on the testing data, it is expected that the automated plain radiograph-based BMD estimation method would be valuable for osteoporosis identification. Osteoporosis is under-detected due to the under-application (or limited availability) of DXA in asymptomatic patients with osteoporosis. Therefore, a tool designed to detect osteoporosis from plain radiographs may improve the chance of at-risk patients being screened and referred for definitive therapy. In areas with limited DXA availability, because the availability of plain radiographs is much larger than the availability of DXA, the plain radiograph-based BMD estimation method may serve as the primary tool for identifying patients at risk of osteoporosis totally automatically and with high reproducibility.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer-readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a device for performing the operations herein. This device may be specially constructed for the required purposes, or it may comprise a general-purpose computer selectively activated or reconfigured by a computer program stored in the computer. Such a computer program may be stored in a computer-readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

What is claimed is:

1. A computer-implemented method for radiographic bone mineral density (BMD) estimation, the method comprising:
    receiving a plain radiograph;
    detecting landmarks for a bone structure included in the plain radiograph;
    extracting a region of interest (ROI) from the plain radiograph based on the detected landmarks, comprising:
        detecting anatomical landmarks at a center of the femur head when detecting the landmarks included in the plain radiograph for the bone structure;
        determining a size of the ROI relevant to a distance between two femur heads, wherein the ROI is a rectangular region containing a femur head, a greater trochanter, and a lesser trochanter, segmented from the plain radiograph; and
        determining a center of the ROI based on locations of the femur heads; and
    estimating the BMD for the ROI extracted from the plain radiograph by using a deep neural network.

2. The method according to claim 1, wherein detecting the anatomical landmarks at the center of the femur head comprises:
    generating a feature map for the plain radiograph via a convolutional neural network;
        initializing an initial graph based on the generated feature map, the initial graph representing initial landmarks of the femur head;
        performing a global graph convolution of the initial graph to generate a global graph, wherein landmarks in the global graph move closer to target locations associated with the femur head; and
        iteratively performing a local graph convolution of the global graph to generate a series of local graphs, wherein landmarks in the series of local graphs iteratively move further towards the target locations associated with the femur head.

3. The method according to claim 1, wherein extracting the ROI from the plain radiograph further includes:
    segmenting the femur head, the greater trochanter, and the lesser trochanter from the plain radiograph using a contour transformer network; and
    determining a size and a location of the ROI to cover the detected femur head, the greater trochanter, and the lesser trochanter.

4. A device for radiographic bone mineral density (BMD) estimation, comprising:
    a processor; and
    a memory communicatively coupled to the processor, the memory storing computer programs that, when executed by the processor, cause the processor to implement the method according to claim 1.

5. A computer program product comprising a non-transitory computer-readable storage medium and program instructions stored therein, the program instructions being configured to be executable by a computer to cause the computer to implement the method according to claim 1.

6. A computer-implemented method for radiographic bone mineral density (BMD) estimation, the method comprising:
    receiving a plain radiograph;
    detecting landmarks for a bone structure included in the plain radiograph;
    extracting a region of interest (ROI) from the plain radiograph based on the detected landmarks;

performing a quality assessment of the ROI to determine whether the ROI is applicable for BMD estimation, wherein the quality assessment comprises:
  detecting whether there is a hip fracture in the ROI; and
  in response to a hip fracture being in the ROI, excluding the ROI with the hip fracture from the BMD estimation; and
estimating the BMD for the ROI extracted from the plain radiograph by using a deep neural network.

7. The method according to claim 6, wherein detecting whether there is the hip fracture in the ROI comprises:
  pre-processing the plain radiograph to produce an input image, a flipped image, and a spatial alignment transformation corresponding to the input image and the flipped image;
  performing Siamese encoding on the input image to produce an encoded input feature map;
  performing Siamese encoding on the flipped image to produce an encoded flipped feature map;
  performing a feature alignment using the spatial alignment transformation on the encoded flipped feature map to produce an encoded symmetric feature map; and
  processing the encoded input feature map and the encoded symmetric feature map to generate a diagnostic result indicating a presence and a location of the hip fracture in the ROI.

8. A device for radiographic bone mineral density (BMD) estimation, comprising:
  a processor; and
  a memory communicatively coupled to the processor, the memory storing computer programs that, when executed by the processor, cause the processor to implement the method according to claim 6.

9. A computer program product comprising a non-transitory computer-readable storage medium and program instructions stored therein, the program instructions being configured to be executable by a computer to cause the computer to implement the method according to claim 6.

10. A computer-implemented method for radiographic bone mineral density (BMD) estimation, the method comprising:
  receiving a plain radiograph;
  detecting landmarks for a bone structure included in the plain radiograph;
  extracting a region of interest (ROI) from the plain radiograph based on the detected landmarks; and
  estimating the BMD for the ROI extracted from the plain radiograph by using a deep neural network, wherein:
  the plain radiograph is a lateral spine X-ray image for L1-L4 vertebrae of a human,
  a quality assessment includes a detection of an existence of a compression vertebral fracture (VCF), a bone cement injection, and a spinal implant, and
  the VCF, the bone cement injection, and the spinal implant are detected using a trained neural network.

11. The method according to claim 10, wherein the deep neural network is trained to estimate the BMDs of L1-L4 vertebrae from corresponding ROIs.

12. The method according to claim 10, wherein the ROI is a rectangular region containing a body of a vertebra and a spinous process.

13. The method according to claim 12, wherein the ROI is defined based on four landmarks at an anterior point and a posterior point of upper and inferior endplates of the vertebra.

14. The method according to claim 13, wherein the four landmarks are selected from six landmarks detected from a landmark detection process, the six landmarks comprising landmarks of an anterior point, a middle point, and a posterior point of upper and inferior endplates of the vertebra.

15. The method according to claim 10, wherein the VCF is further detected using a six-point morphometry criterion based on six landmarks at an anterior point, a middle point, and a posterior point of upper and inferior endplates of a vertebra.

16. The method according to claim 15, wherein the six landmarks are detected by:
  generating a feature map for the plain radiograph via a convolutional neural network;
  initializing an initial graph based on the generated feature map, the initial graph representing initial landmarks of an anterior point, a middle point, and a posterior point of upper and inferior endplates of the vertebra;
  performing a global graph convolution of the initial graph to generate a global graph, wherein landmarks in the global graph move closer to target locations associated with the anterior point, the middle point, and the posterior point of the upper and inferior endplates of the vertebra; and
  iteratively performing a local graph convolution of the global graph to generate a series of local graphs, wherein landmarks in the series of local graphs iteratively move further towards the target locations associated with the anterior point, the middle point, and the posterior point of the upper and inferior endplates of the vertebra.

17. A device for radiographic bone mineral density (BMD) estimation, comprising:
  a processor; and
  a memory communicatively coupled to the processor, the memory storing computer programs that, when executed by the processor, cause the processor to implement the method according to claim 10.

18. A computer program product comprising a non-transitory computer-readable storage medium and program instructions stored therein, the program instructions being configured to be executable by a computer to cause the computer to implement the method according to claim 10.

* * * * *